United States Patent
Reading et al.

(10) Patent No.: US 10,799,446 B2
(45) Date of Patent: Oct. 13, 2020

(54) TIME-RELEASE AND MICRO-DOSE FORMULATIONS FOR TOPICAL APPLICATION OF ESTROGEN AND ESTROGEN ANALOGS OR OTHER ESTROGEN RECEPTOR MODULATORS IN THE TREATMENT OF DRY EYE SYNDROME, AND METHODS OF PREPARATION AND APPLICATION

(71) Applicant: Redwood Pharma AB, Stockholm (SE)

(72) Inventors: Clive H. Reading, Kent (GB); Thomas Rowe, Roswell, GA (US); Mario G. Fsadni, Hertfordshire (GB); Richard Coulon, Cummings, GA (US)

(73) Assignee: REDWOOD PHARMA AB, Stockholm (SE)

( * ) Notice: Subject to any disclaimer, the term of this patent is extended or adjusted under 35 U.S.C. 154(b) by 133 days.

(21) Appl. No.: 15/985,554

(22) Filed: May 21, 2018

(65) Prior Publication Data

US 2018/0263901 A1    Sep. 20, 2018

Related U.S. Application Data

(60) Division of application No. 14/618,355, filed on Feb. 10, 2015, now abandoned, which is a continuation of application No. 13/378,335, filed as application No. PCT/US2010/039250 on Jun. 18, 2010, now Pat. No. 8,987,241.

(60) Provisional application No. 61/218,899, filed on Jun. 19, 2009.

(51) Int. Cl.

| | |
|---|---|
| A61K 9/00 | (2006.01) |
| A61K 31/568 | (2006.01) |
| A61K 31/5685 | (2006.01) |
| A61K 45/06 | (2006.01) |
| A61K 47/32 | (2006.01) |
| A61K 47/36 | (2006.01) |
| A61K 47/40 | (2006.01) |
| A61K 31/565 | (2006.01) |
| A61K 31/566 | (2006.01) |

(52) U.S. Cl.
CPC .......... *A61K 9/0048* (2013.01); *A61K 31/565* (2013.01); *A61K 31/566* (2013.01); *A61K 31/568* (2013.01); *A61K 31/5685* (2013.01); *A61K 45/06* (2013.01); *A61K 47/32* (2013.01); *A61K 47/36* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 4,474,571 | A | 10/1984 | Haslam et al. |
| 4,478,818 | A | 10/1984 | Shell et al. |
| 4,730,013 | A | 3/1988 | Bondi et al. |
| 4,738,851 | A | 4/1988 | Schoenwald et al. |
| 4,853,224 | A | 8/1989 | Wong |
| 4,997,652 | A | 3/1991 | Wong |
| 5,164,188 | A | 11/1992 | Wong |
| RE34,578 | E | 4/1994 | Lubkin |
| 5,443,505 | A | 8/1995 | Wong et al. |
| 5,662,931 | A | 9/1997 | Munechika et al. |
| 5,766,242 | A | 6/1998 | Wong et al. |
| 5,770,628 | A | 6/1998 | Cantoro |
| 6,096,733 | A | 8/2000 | Lubkin |
| 6,656,460 | B2 | 12/2003 | Benita et al. |
| 7,048,946 | B1 | 5/2006 | Wong et al. |
| 7,204,995 | B2 | 4/2007 | El-Sherif et al. |
| 8,987,241 | B2 * | 3/2015 | Reading ............ A61K 45/06 514/182 |
| 2006/0111318 | A1 | 5/2006 | Okamoto |
| 2006/0211660 | A1 | 9/2006 | Du Mee et al. |

FOREIGN PATENT DOCUMENTS

| | | |
|---|---|---|
| EP | 1621199 | 2/2006 |
| WO | WO 2006-094026 | 9/2006 |
| WO | WO 2006/094028 | 9/2006 |

OTHER PUBLICATIONS

German et al, "Reliability of drop size from multi-dose eye drop bottles: is it cause for concern?," Eye, vol. 13, No. 1, pp. 93-100 (Year: 1999).*

Conway, Barbara R., "Recent Patents on Ocular Drug Delivery Systems", Recent Patents on Drug Delivery and Formulation, vol. 2, No. 1, 2008, pp. 1-8.

del Amo et al., "Current and Future Ophthalmic Drug Delivery Systems. A Shift to the Posterior Segment.", Drug Discovery Today, vol. 13, No. 3/4, Feb. 2008, pp. 135-143.

(Continued)

*Primary Examiner* — Dennis J Parad

(74) *Attorney, Agent, or Firm* — James S. Keddie; Bozicevic, Field & Francis LLP

(57) ABSTRACT

A topical application formulation of estrogen and estrogen analogs or other estrogen receptor modulators is disclosed for the treatment of primary or secondary dry eye syndrome (also known as keratoconjunctivitis sicca (KCS)). Preferred formulations include 17-β-estradiol and its derivatives in lipid, liposomes, polymers, or aqueous or non-aqueous vehicles for the topical treatment of the ocular surface tissues particularly as time-release or micro-dose formulations. These formulations may also be useful in treating other conditions where KCS may occur, such as post-operative refractive surgery and corneal transplant patients.

10 Claims, 14 Drawing Sheets

(56) References Cited

OTHER PUBLICATIONS

Murube et al., "Classification of Artificial Tears. 1: Composition and Properties", Lacrimal Gland, Tear Film, and Dry Eye Syndromes 2, Advances in Experimental Medicine and Biology, vol. 438, 1998, pp. 693-704.

International Preliminary Report on Patentability received for PCT Patent Application No. PCT/US2010/039250, dated Jan. 5, 2012, 14 pages.

International Search Report and Written Opinion received for PCT Patent Application No. PCT/US2010/039250, dated Oct. 26, 2010, 20 pages.

Prause, J. U., "Treatment of Keratoconjunctivitis Sicca With Lacrisert", Scandinavian Journal of Rheumatology Supplement, vol. 61, 1986, pp. 261-263.

Tuft et al., "Medical Management of Dry Eye Disease", Geerling G, Brewitt H (eds): Surgery for the Dry Eye, Dev. Ophthalmol., Basel, Karger, vol. 41, 2008, pp. 54-74.

Burgalassi et al., "Xyloglucan as a Novel Vehicle for Timolol: Pharmacokinetics and Pressure Lowering Activity in Rabbits", Journal of Ocular Pharmacology and Therapeutics, vol. 16, No. 6, 2000, pp. 497-509.

Ferno et al., "High Molecular Weight Enzyme Inhibitors, III. Polyestradiol Phosphate (P.E.P), a Long-acting Estrogen.", Acta. Chem. Scand., vol. 12, No. 8, 1958, pp. 1675-1689.

Knepper et al., "Effect of Dexamethasone, Progesterone, and Testosterone on IOP and GAGs in the Rabbit Eye", Investigative Ophthalmology & Visual Science, vol. 26, Aug. 1985, pp. 1093-1100.

Margalit, Rimona, "Liposome-Mediated Drug Targeting in Topical and Regional Therapies.", Critical Reviews in Therapeutic Drug Carrier Systems, vol. 12, No. 2 & 3, 1995, pp. 233-261.

Oprea et al., "Hormonal Regulatory Influence in Tear Film", Journal Francais Ophtalmologie, vol. 27, No. 8, Oct. 2004, pp. 933-941.

Reimer et al., "Povidone-Iodine Liposomes—An Overview", Dermatology, vol. 195, Suppl. 2, 1997, pp. 93-99.

Rowe et al., "Measurement and Prediction of Timolol Diffusion with and Without Simulated Tear Flow", Invest. Ophthalmol. Vis. Sci., vol. 51, E-Abstract 2452, 2010, 2 pages.

\* cited by examiner

TIME-RELEASE AND MICRO-DOSE FORMULATIONS FOR TOPICAL APPLICATION OF ESTROGEN AND ESTROGEN ANALOGS OR OTHER ESTROGEN RECEPTOR MODULATORS IN THE TREATMENT OF DRY EYE SYNDROME, AND METHODS OF PREPARATION AND APPLICATION

CROSS-REFERENCING

This application is a divisional of U.S. application Ser. No. 14/618,355, filed on Feb. 10, 2015, which is a continuation of U.S. application Ser. No. 13/378,335, filed on Mar. 19, 2012, now issued as U.S. Pat. No. 8,987,241, which is a § 371 national phase of International Application No. PCT/US2010/039250, filed on Jun. 18, 2010, which claims the benefit of U.S. Application No. 61/218,899, filed on Jun. 19, 2009, which applications are incorporated by reference herein.

BACKGROUND OF THE INVENTION

1. Field

This invention relates to the topical application of estrogen and estrogen analogs and other estrogen receptor modulators in the treatment of primary or secondary dry eye syndrome (also known as keratoconjunctivitis sicca (KCS)) and, in certain embodiments, to the preparation and application of 17-β-estradiol and its derivatives in lipid, liposomes, polymers, or aqueous or non-aqueous vehicles for the topical treatment of the ocular surface tissues particularly as time-release or micro-dose formulations. This invention may also be useful in treating other conditions where KCS may occur, such as post-operative refractive surgery and corneal transplant patients.

2. Related Art

The high incidence of keratoconjunctivitis sicca in the population of postmenopausal women is attended by symptoms ranging from mild foreign body sensation to frank pain and visual loss due to ocular surface abnormalities.

It is known that tear film quality depends on fine regulatory mechanisms affected by neuronal and hormonal influences. Indeed, receptors for androgens, estrogens, progesterone and prolactin have been identified in several ocular tissues in the rat, rabbit and in humans. These hormones influence the immune system, the morphology and secretory functions of lacrimal glands, the morphology and function of the conjunctiva, and the functioning of Meibomian glands. The influence of hormone replacement therapy in menopausal women remains unclear, as some authors support the idea that hormones improve the quality and the volume of tear film, whereas others have argued that they increase the risk of dry eye. Finally, knowledge of the interactions between the hormones that influence the function of the lacrimal gland is an essential element for the understanding of the regulation of lacrimal gland function. Additional data suggest that optimal bioavailable androgen levels are essential for normal lacrimal gland function and that prolactin and estrogens also play important roles in providing a hormonal milieu that contributes to normal lacrimal gland function (Oprea, L., Tiberghien, A., Creuzot-Garcher. C., Baudouin, C., *Hormonal Regulatory Influence in Tear Film*, J. Fr. Ophtalmol., October 27(8):93341 (2004)).

The standard treatment with artificial lubricants provides temporary symptomatic relief in most cases, but does not address the cause of the dry eyes. While there has been described treatment of post menopausal females with dry eye syndrome using oral Premarin therapy, the oral or parenteral administration of estrogen can frequently produce side effects such as vaginal bleeding, breast tenderness and other undesired effects and the therapeutic effects derived from oral therapy do not justify the risk. Further, such oral, dermal (e.g., application to the skin of the outer eyelid) or parenteral administration implicates the entire body structure in an indeterminate effort to secure an effect in a localized area (the eye), in the absence of any data relating the level of estrogen introduced into the blood stream to the level, if any, resulting in the tear fluid (it is known generally, that estrogen concentrations in the eye to be in the range of about 10% of serum levels). Conservative medicine would indicate the desirability of limiting the specific effect of the hormone to the target site if possible.

As the data in U.S. Pat. No. 6,096,733 demonstrates, the effective concentration of 17-β-estradiol in solution can be as low as 0.1% and continue to be effective regardless of the presence or absence of concomitant oral estrogen therapy in post-menopausal women. This lower dose range is especially useful in providing eye drops that will contain a concentration of 17-β-estradiol that is low enough to be both safe and effective (the medical aspect) yet has the potential to be approved by the FDA for use in non-prescription (OTC) based formulations (the commercial aspect). However, the low dose of 0.1% was applied three or four times per day in U.S. Pat. No. 6,096,733. Thus, U.S. Pat. No. 6,096,733, while providing a low dose formulation, did not provide examples of a time release or micro-dose formulation that could be used only at lower frequency.

In addition, the low dose formulation in the U.S. Pat. No. 6,096,733 exhibits side effect due to systemic effects of the 17-β-estradiol administered topically. When a lower does (0.05% 17-β-estradiol) was tested in a Phase IIb trial, it showed lower efficacy than the 0.1% dose for all but one of the signs and symptoms recorded for the trial. Thus, there is a need for formulations that can provide an efficacious dose without the systemic side effects, preferably with a lower frequency of dosing.

BRIEF SUMMARY OF THE INVENTION

Accordingly, it is a principal object of this invention to provide treatment by topical application of 17-β-estradiol suspended or dissolved or otherwise incorporated in a suitable vehicle formulated for long-term release and/or microdose to the conjunctival surface of the eye, the inner eyelid or the outer eyelid to alleviate dry-eye syndrome or KCS that need be delivered only at twice per day or lower frequency while retaining full efficacy. Surprisingly, these timed release formulations are efficacious at a much lower dose than the formulation provided in U.S. Pat. No. 6,096,733. Thus, these novel formulations meet both needs by providing an efficacious dose without the systemic side effects and by providing a sustained release profile that allows a lower dose frequency.

One aspect of the invention includes a topical application pharmaceutical composition for timed release comprising estrogen or an estrogen analog wherein the timed release is sufficient for delivery of a therapeutically effective concentration for alleviation of kerato-conjunctivitis sicca (dry eye syndrome) when administered twice daily or less frequently. In certain embodiments, the pharmaceutical is in the form of a semi-solid insert for the cul-de-sac of the eye, a gel, or a semi-solid ointment. In other embodiments which may be combined with the preceding embodiments, the topical application pharmaceutical includes a bioadhesive viscoelastic compound. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release is sufficient for delivery of a therapeutically effective concentration for alleviation of kerato-conjunctivitis sicca (dry eye syndrome) when administered once per day or less frequently, every other day or less frequently, every third day or less frequently or once per week or less frequently. In other embodiments which may be combined with the preceding embodiments, the timed release is sufficient for delivery of a therapeutically effective concentration for alleviation of kerato-conjunctivitis sicca (dry eye syndrome) when administered once per day, every other day, every third day or once per week. In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers a dose of between 0.1 pg and 1.0 pg of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the estrogen analog is 17-β-estradiol. In other embodiments which may be combined with the preceding embodiments, the therapeutically effective amount is between about 0.005% and 5% weight-by-weight of estrogen or the estrogen analog. In other embodiments which may be combined with the preceding embodiments, the therapeutically effective amount is between about 0.005% and about 0.1%, 0.005% and less than 0.05%, 0.01% and about 0.04%, about 0.05% and about 0.5%, about 0.05% and about 0.1%, about 0.1% and about 5%, about 0.5% and 5%, and less than or equal to 0.1%. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments which may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the topical application pharmaceutical further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandro-sterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Another aspect of the invention includes a topical application pharmaceutical composition for timed release comprising 17-beta-estradiol or a derivative thereof at a concentration of less than 0.05% wherein the timed release is sufficient for delivery of a therapeutically effective concentration for alleviation of kerato-conjunctivitis sicca (dry eye syndrome) when administered twice daily or less frequently. In certain embodiments, the pharmaceutical is in the form of a semi-solid insert for the cul-de-sac of the eye, a gel, or a semi-solid ointment. In other embodiments which may be combined with the preceding embodiments, the topical application pharmaceutical includes a bioadhesive viscoelastic compound. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release is sufficient for delivery of a therapeutically effective concentration for alleviation of kerato-conjunctivitis sicca (dry eye syndrome) when administered once per day or less frequently, every other day or less frequently, every third day or less frequently or once per week or less frequently. In other embodiments which may be combined with the preceding embodiments, the timed release is sufficient for delivery of a therapeutically effective concentration for alleviation of kerato-conjunctivitis sicca (dry eye syndrome) when administered once per day, every other day, every third day or once per week. In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers a dose of between 0.1 pg and 1.0 pg of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the estrogen analog is 17-β-estradiol. In other embodiments which may be combined with the preceding embodiments, the therapeutically effective amount is between about 0.005% and less than 0.05% weight-by-weight of estrogen or the estrogen analog. In other embodiments which may be combined with the preceding embodiments, the therapeutically effective amount is between about 0.01% and less than 0.04%, 0.005% and about 0.04%, and 0.01% and about 0.04%. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments which may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the topical application pharmaceutical further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandro-sterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Yet another aspect of the invention includes methods of treatment comprising topical application to an eye of a topical application pharmaceutical according to either of the two preceding aspects with any of their respective combinations of embodiments. In certain embodiments, the kerato-conjunctivitis sicca is associated with post-menopausal subjects, post-operative refractive surgery patients or corneal transplant patients.

Still another aspect of the invention includes use of a topical application pharmaceutical according to either of the two preceding topical application pharmaceutical composition aspects with any of their respective combinations of embodiments in the manufacture of a medicament for alleviation of kerato-conjunctivitis sicca (dry eye syndrome). In certain embodiments, the kerat-conjunctivitis sicca is associated with post-menopausal subjects, post-operative refractive surgery patients or corneal transplant patients.

Another aspect of the invention includes methods of alleviation of kerato-conjunctivitis sicca (dry eye syndrome) comprising administering by topical application a therapeutically effective dose to an eye of a topical application pharmaceutical, wherein the therapeutically effective dose comprises a volume of less than a standard ophthalmic drop and wherein the therapeutically effective dose less than 35 micrograms of estrogen or an estrogen analog. In certain embodiments, the volume is less than 35 µl, less than 30 µl, less than 25 µl, less than 20 µl, less than 15 µl, or between 5 µl and 15 µl. In other embodiments that may be combined with the preceding embodiments, the dose is less 30 micrograms, less 25 micrograms, less 20 micrograms, less 15 micrograms, or less 10 micrograms of estrogen or an estrogen analog. In other embodiments that may be combined with the preceding embodiments, the topical application pharmaceutical is administered twice daily or less frequently. In other embodiments that may be combined with the preceding embodiments, the pharmaceutical is in the form of a semi-solid insert for the cul-de-sac of the eye, a gel, or a semi-solid ointment. In other embodiments that may be combined with the preceding embodiments, the topical application pharmaceutical is administered once per day or less frequently, every other day or less frequently, every third day or less frequently or once per week or less frequently. In other embodiments that may be combined with the preceding embodiments, the topical application pharmaceutical is administered once per day, every other day, every third day or once per week. In other embodiments that may be combined with the preceding embodiments, the estrogen analog is 17-β-estradiol. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments that may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the method includes a bioadhesive viscoelastic compound for timed release of the estrogen or estrogen analog. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, the sustained drug release rate which delivers a dose of between 0.1 pg and 1.0 pg of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the method further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandrosterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Still another aspect includes methods of alleviation of kerato-conjunctivitis sicca (dry eye syndrome) comprising administering by topical application a therapeutically effective dose to an eye of a topical application pharmaceutical, wherein the therapeutically effective dose comprises a volume of less than 35 µl and wherein the therapeutically effective dose less than 35 micrograms of 17-beta-estradiol or a derivative. In certain embodiments, the volume is less than 30 µl, less than 25 µl, less than 20 µl, less than 15 µl, or between 5 µl and 15 µl. In other embodiments that may be combined with the preceding embodiments, the dose is less 30 micrograms, less 25 micrograms, less 20 micrograms, less 15 micrograms, or less 10 micrograms of estrogen or an estrogen analog. In other embodiments that may be combined with the preceding embodiments, the topical application pharmaceutical is administered twice daily or less frequently. In other embodiments that may be combined with the preceding embodiments, the pharmaceutical is in the form of a semi-solid insert for the cul-de-sac of the eye, a gel, or a semi-solid ointment. In other embodiments that may be combined with the preceding embodiments, the topical application pharmaceutical is administered once per day or less frequently, every other day or less frequently, every third day or less frequently or once per week or less frequently. In other embodiments that may be combined with the preceding embodiments, the topical application pharmaceutical is administered once per day, every other day, every third day or once per week. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments that may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the method includes a bioadhesive viscoelastic compound for timed release of the estrogen or estrogen analog. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers a dose of between 0.1 pg and 1.0 pg of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the method further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandrosterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Yet another aspect includes use of a topical application pharmaceutical for use in either of the two preceding aspects with any of their respective combinations of embodiments in the manufacture of a medicament for alleviation of kerato-conjunctivitis sicca (dry eye syndrome). In certain embodiments, the kerato-conjunctivitis sicca is associated with post-menopausal subjects, post-operative refractive surgery patients or corneal transplant patients.

Another aspect of the invention includes a topical application pharmaceutical composition for timed release comprising estrogen or an estrogen analog or other estrogen receptor modulator wherein the timed release is sufficient for delivery of a therapeutically effective concentration for alleviation of kerato-conjunctivitis sicca (dry eye syndrome) when administered twice daily or less frequently. In certain embodiments, the pharmaceutical is in the form of a semi-solid insert for the cul-de-sac of the eye, a gel, or a semi-solid ointment. In other embodiments which may be combined with the preceding embodiments, the topical application pharmaceutical includes a bioadhesive viscoelastic compound. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release is sufficient for delivery of a therapeutically effective concentration for alleviation of kerato-conjunctivitis sicca (dry eye syndrome) when administered once per day or less frequently, every other day or less frequently, every third day or less frequently or once per week or less frequently. In other embodiments which may be combined with the preceding embodiments, the timed release is sufficient for delivery of a therapeutically effective concentration for alleviation of kerato-conjunctivitis sicca (dry eye syndrome) when administered once per day, every other day, every third day or once per week. In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers a dose of between 0.1 pg and 1.0 pg of estrogen or the estrogen analog or other estrogen receptor modulator per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the estrogen analog is 17-β-estradiol. In other embodiments which may be combined with the preceding embodiments, the therapeutically effective amount is between about 0.005% and 5% weight-by-weight of estrogen or the estrogen analog or other estrogen receptor modulator. In other embodiments which may be combined with the preceding embodiments, the therapeutically effective amount is between about 0.005% and about 0.1%, 0.005% and less than 0.05%, 0.01% and about 0.04%, about 0.05% and about 0.5%, about 0.05% and about 0.1%, about 0.1% and about 5%, about 0.5% and 5%, and less than or equal to 0.1%. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments which may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the topical application pharmaceutical further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandrosterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Yet another aspect of the invention includes methods of treatment comprising topical application to an eye of a topical application pharmaceutical according to the preceding aspect with any of its respective combinations of embodiments. In certain embodiments, the kerato-conjunctivitis sicca is associated with post-menopausal subjects, subjects with premature ovarian failure, post-operative refractive surgery patients, corneal transplant patients or patients with other conditions that cause dry eye symptoms.

Still another aspect of the invention includes use of a topical application pharmaceutical according to the two preceding topical application pharmaceutical composition aspect with any of its respective combinations of embodiments in the manufacture of a medicament for alleviation of kerato-conjunctivitis sicca (dry eye syndrome). In certain embodiments, the kerato-conjunctivitis sicca is associated with post-menopausal subjects, premature ovarian failure, post-operative refractive surgery patients, corneal transplant patients or patients with other conditions that cause dry eye symptoms.

Another aspect of the invention includes methods of alleviation of kerato-conjunctivitis sicca (dry eye syndrome) comprising administering by topical application a therapeutically effective dose to an eye of a topical application pharmaceutical, wherein the therapeutically effective dose comprises a volume of less than a standard ophthalmic drop and wherein the therapeutically effective dose less than 35 micrograms of estrogen or an estrogen analog or other estrogen receptor modulator. In certain embodiments, the volume is less than 35 μl, less than 30 μl, less than 25 μl, less than 20 μl, less than 15 μl, or between 5 μl and 15 μl. In other embodiments that may be combined with the preceding embodiments, the dose is less 30 micrograms, less 25 micrograms, less 20 micrograms, less 15 micrograms, or less 10 micrograms of estrogen or an estrogen analog or other estrogen receptor modulator. In other embodiments that may be combined with the preceding embodiments, the topical application pharmaceutical is administered twice daily or less frequently. In other embodiments that may be combined with the preceding embodiments, the pharmaceutical is in the form of a semi-solid insert for the cul-de-sac of the eye, a gel, or a semi-solid ointment. In other embodiments that may be combined with the preceding embodiments, the topical application pharmaceutical is administered once per day or less frequently, every other day or less frequently, every third day or less frequently or once per week or less frequently. In other embodiments that may be combined with the preceding embodiments, the topical application pharmaceutical is administered once per day, every other day, every third day or once per week. In other embodiments that may be combined with the preceding embodiments, the estrogen analog is 17-β-estradiol. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments that may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the method includes a bioadhesive viscoelastic compound for timed release of the estrogen or estrogen analog or other estrogen receptor modulator. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, the sustained drug release rate which delivers a dose of between 0.1 pg and 1.0 pg of estrogen or the estrogen analog or other estrogen receptor modulator per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the method further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandrosterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Still another aspect includes methods of alleviation of kerato-conjunctivitis sicca (dry eye syndrome) comprising administering by topical application a therapeutically effective dose to an eye of a topical application pharmaceutical, wherein the therapeutically effective dose comprises a volume of less than 35 µl and wherein the therapeutically effective dose less than 35 micrograms of 17-beta-estradiol or a derivative. In certain embodiments, the volume is less than 30 µl, less than 25 µl, less than 20 µl, less than 15 µl, or between 5 µl and 15 µl. In other embodiments that may be combined with the preceding embodiments, the dose is less 30 micrograms, less 25 micrograms, less 20 micrograms, less 15 micrograms, or less 10 micrograms of estrogen or an estrogen analog or other estrogen receptor modulator. In other embodiments that may be combined with the preceding embodiments, the topical application pharmaceutical is administered twice daily or less frequently. In other embodiments that may be combined with the preceding embodiments, the pharmaceutical is in the form of a semi-solid insert for the cul-de-sac of the eye, a gel, or a semi-solid ointment. In other embodiments that may be combined with the preceding embodiments, the topical application pharmaceutical is administered once per day or less frequently, every other day or less frequently, every third day or less frequently or once per week or less frequently. In other embodiments that may be combined with the preceding embodiments, the topical application pharmaceutical is administered once per day, every other day, every third day or once per week. In other embodiments which may be combined with the preceding embodiments, the increase in peak blood estradiol concentration after continuous use is less that 30 pg/ml, less than 20 pg/ml, less than 15 pg/ml, less than 10 pg/ml or less than 6 pg/ml. In other embodiments that may be combined with the preceding embodiments, the average blood concentration of estrogen after continuous use is less than 12 m I.U., less than 10 m I.U., less than 8 m I.U., less than 6 m I.U., less than 5 m I.U., less than 4 m I.U., or less than 3 m I.U. In other embodiments which may be combined with the preceding embodiments, the method includes a bioadhesive viscoelastic compound for timed release of the estrogen or estrogen analog or other estrogen receptor modulator. In other embodiments which may be combined with the preceding embodiments that include a bioadhesive viscoelastic compound, the bioadhesive viscoelastic compound is in a concentration sufficient to achieve the timed release. In other embodiments which may be combined with the preceding embodiments that include a bioadhesive viscoelastic compound, the bioadhesive viscoelastic compound is selected from the group consisting of polycarbophil, hyaluronate, chitosan, a polysaccharide and polycarboxylated polymer, carboxyl methyl cellulose, hydroxypropyl methyl cellulose, liposomes, a polysaccharide and a positively-charged submicron emulsion. In other embodiments which may be combined with the preceding embodiments that include a polysaccharide, the polysaccharide is xanthan gum, which optionally can be between about 0.1% to about 1% (w/w) or about 0.6% (w/w). In other embodiments which may be combined with the preceding embodiments that include carboxyl methyl cellulose, the carboxyl methyl cellulose is LACRISERT™. In other embodiments which may be combined with the preceding embodiments that include a positively-charged submicron emulsion, the positively-charged submicron emulsion is NOVASORB™ or CATIONORM™. In other embodiments which may be combined with the preceding embodiments that include liposomes, the liposomes are multi-vesicular. In other embodiments which may be combined with the preceding embodiments that include multi-vesicular liposomes, the multi-vesicular liposomes are DEPOFOAM™. In other embodiments which may be combined with the preceding embodiments that include a polysaccharide and polycarboxylated polymer, the polysaccharide and polycarboxylated polymer is PROLOC™. In other embodiments which may be combined with the preceding embodiments that include a bioadhesive viscoelastic compound, the bioadhesive viscoelastic compound is a carbomer, optionally a carbopol, which optionally is carbopol is carbopol 980 or carbopol 940. The carbomer may be from about 0.5% to about 4% or about 2%. In other embodiments which may be combined with the preceding embodiments, the composition further comprises cyclodextrin, which optionally can be from about 0.1% to about 7% (w/w), from about 0.1% to about 1% (w/w), or about 0.4% (w/w). In other embodiments which may be combined with the preceding embodiments, the timed release comprises a controlled, sustained drug release rate which does not vary by more than about 50% for a period of at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers a dose of between 0.1 pg and 1.0 pg of estrogen or the estrogen analog or other estrogen receptor modulator per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the timed release comprises a controlled, sustained drug release rate which delivers as measured by a Franz diffusion cell model with simulated tear flow a dose of between 0.1 mg/ml and 1.0 mg/ml of estrogen or the estrogen analog per hour at least about 6-8 hours after application, at least about 8-12 hours after application, at least about 12-24 hours after application, at least about 24-48 hours after application, or at least about 48-72 hours after application. In other embodiments which may be combined with the preceding embodiments, the method further includes a therapeutically effective amount of an androgen. In other embodiments which may be combined with the preceding embodiments that include an androgen, the androgen is selected from the group consisting of testosterone, dihydrotestosterone (also termed allodihydrotestosterone, androstanolone, stanolone, 5 alpha-dihydrotestosterone), fluoxymesterone, stanozolol, nortestosterone propionate, dehydroepiandrosterone (an androgen precursor, also termed androstenolone, dehydroisoandrosterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives. In other embodiments which may be combined with the preceding embodiments that include an androgen, the therapeutically effective amount of androgen is sufficient to reduce ocular inflammation.

Yet another aspect includes use of a topical application pharmaceutical for use in either of the two preceding aspects with any of their respective combinations of embodiments in the manufacture of a medicament for alleviation of kerato-conjunctivitis sicca (dry eye syndrome). In certain embodiments, the kerato-conjunctivitis sicca is associated with post-menopausal subjects, premature ovarian failure, post-operative refractive surgery patients, corneal transplant patients or patients with other conditions that cause dry eye symptoms.

DETAILED DESCRIPTION OF THE INVENTION

Time-Release Delivery of Ophthalmic Estradiol Formulations

Figure 1:
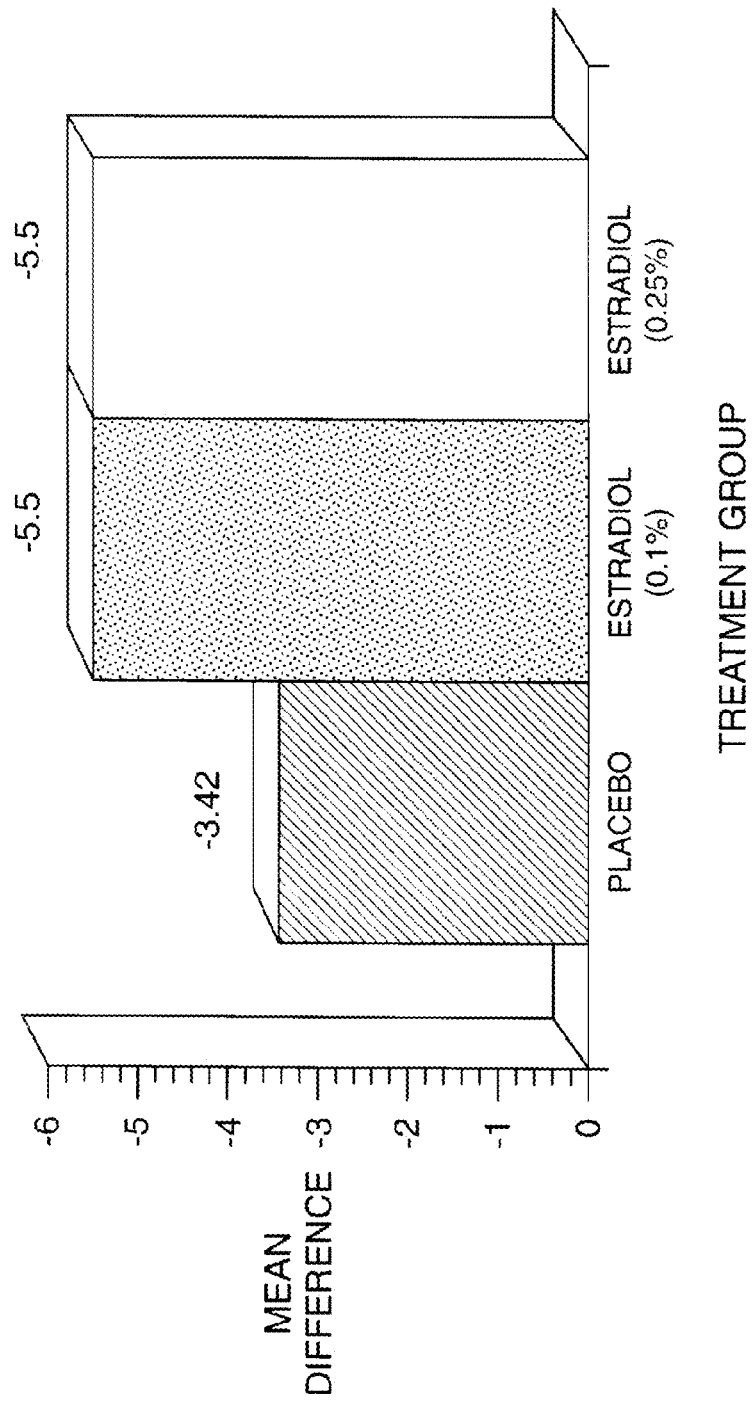
FIG. 1 shows the mean change for total subject scores of the test of a non-time release formulation.
Figure 2:
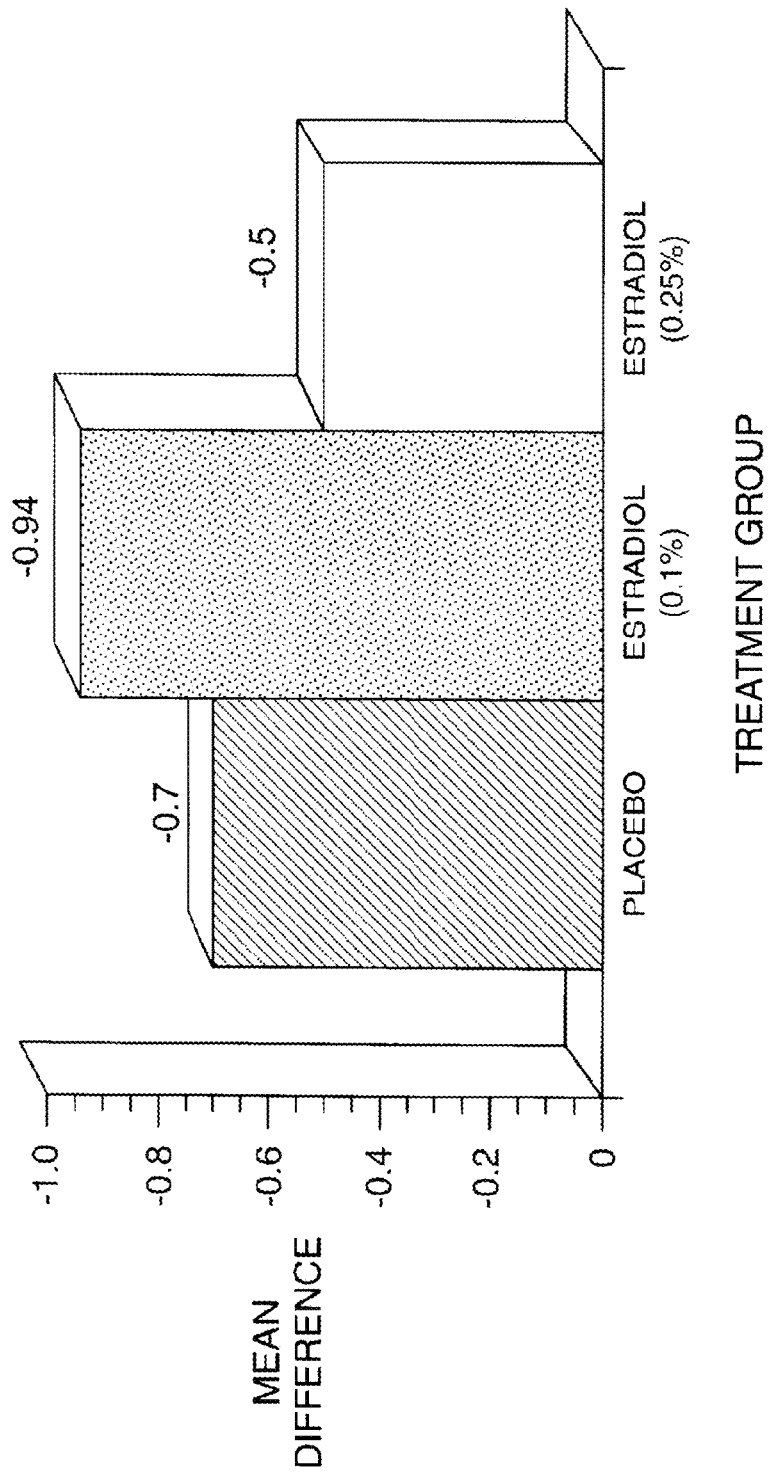
FIG. 2. shows the mean change for SPK testing a non-time release formulation.
Figure 3:
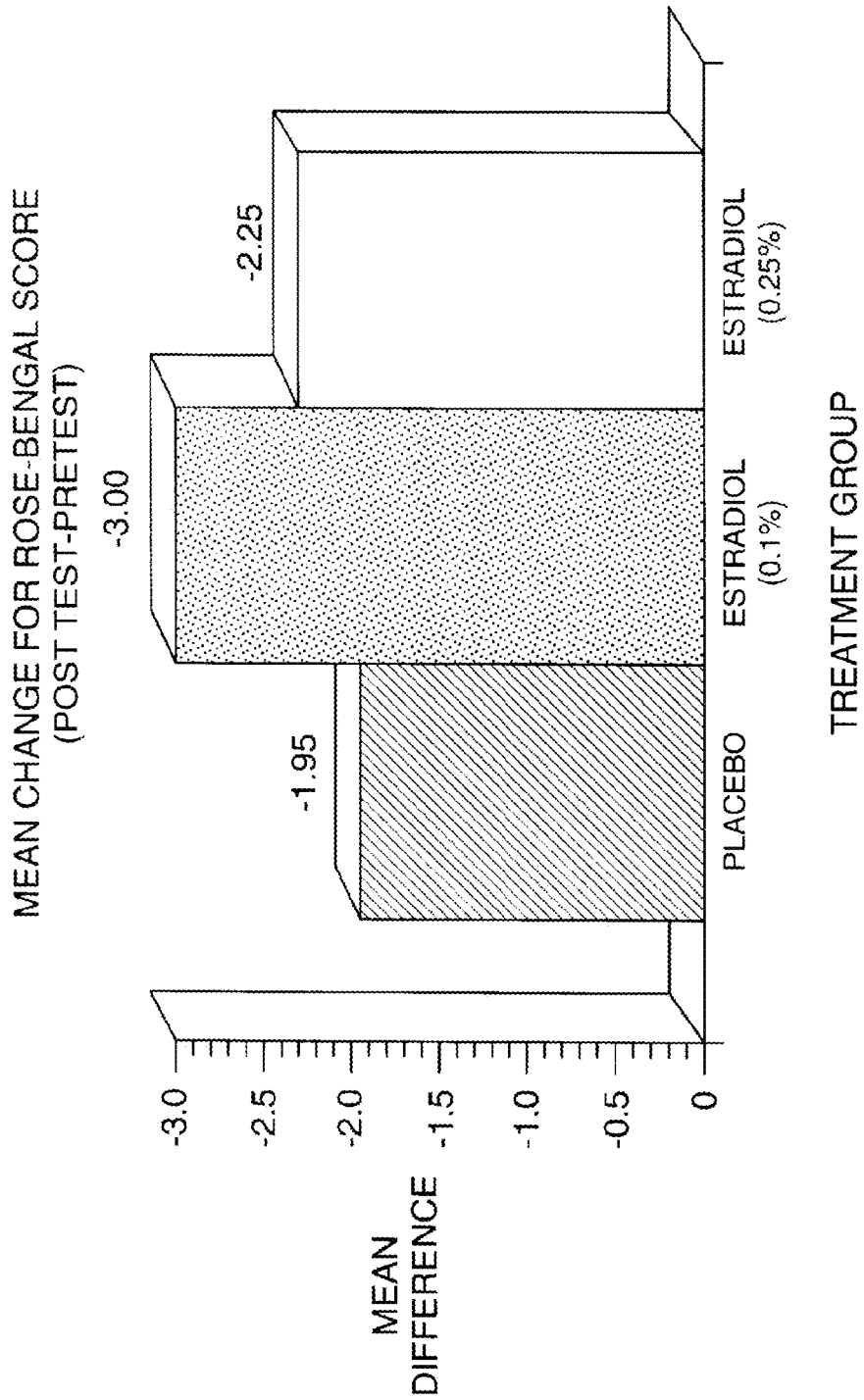
FIG. 3. shows the mean change for the Rose-Bengal testing a non-time release formulation.
Figure 4:
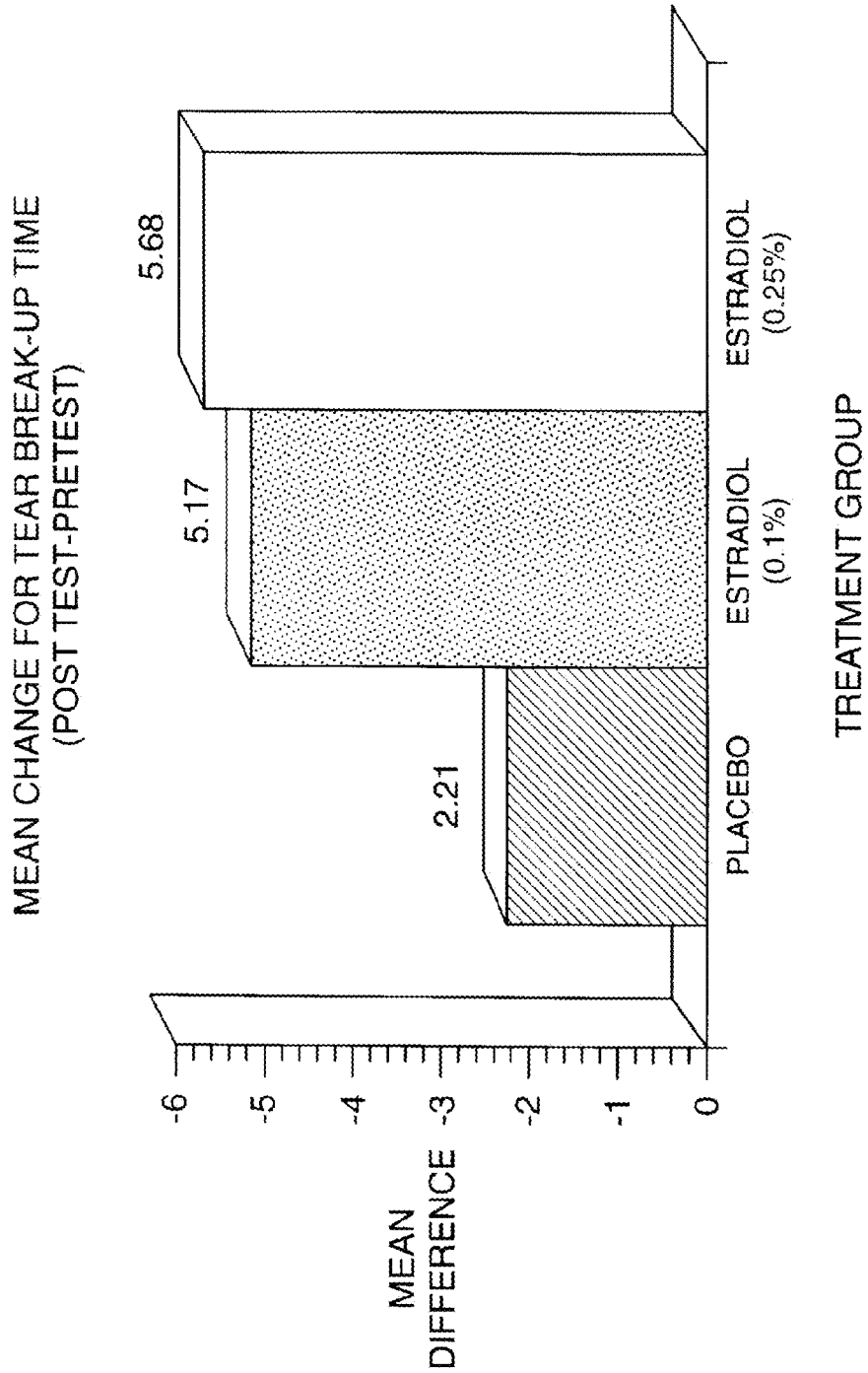
FIG. 4 shows the mean change for the TBUT testing a non-time release formulation.
Figure 5:
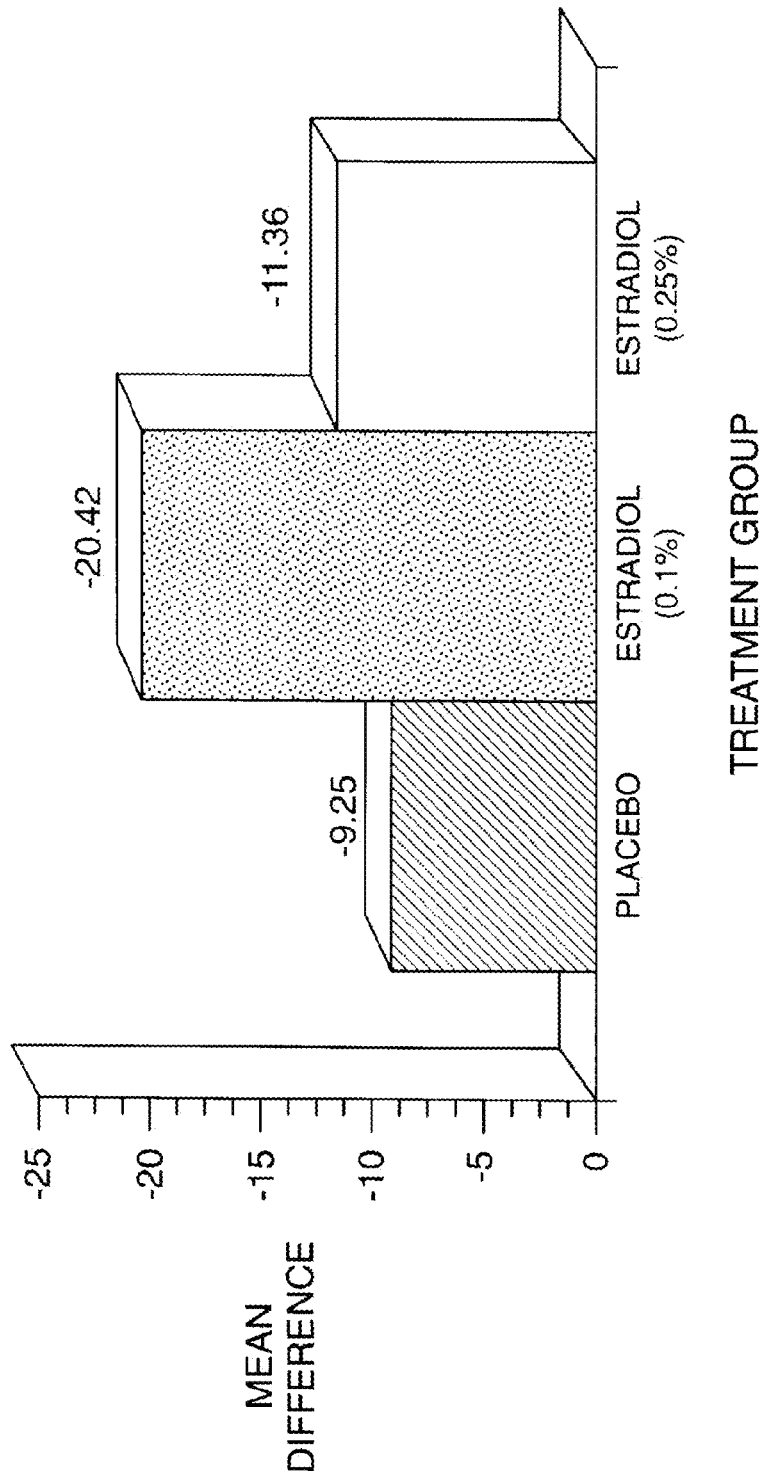
FIG. 5 shows the mean change for Osmolarity a non-time release formulation.

The ophthalmic estradiol formulations for topical administration to the conjunctiva, the inner eyelid or the outer eyelid described herein may be conveniently admixed with a non-toxic pharmaceutical organic carrier, or with a non-toxic pharmaceutical inorganic carrier that provides for timed release of the estrogen or estrogen analog or other estrogen receptor modulator. These ophthalmic formulations are based upon the surprising finding that these timed release formulations deliver efficacious doses of estradiol at significantly lower concentrations over a longer period of time as compared to prior formulations. These new timed release formulations therefore address current needs: the dosing frequency is lower, which can improve patient compliance, and the overall concentration is lower, which can avoid systemic side effects of the estradiol.

Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The ophthalmic estradiol formulations may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, oxychloro complex-buffering ingredients such as sodium borate, sodium acetates, gluconate buffers, and other conventional ingredients such as sorbitan monolaurate, triethanolamine, oleate, polyoxyethylene sorbitan monopailitylate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The ophthalmic estradiol formulations may also be in the form of a micro- or nano-particle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol (e.g., carbopol 980 or carbopol 940, in each case from about 0.5% to about 4% (w/w)) and xanthan gum (e.g., about 0.1% to about 1% (w/w)), gellan gum, and mixtures of said polymer. In some embodiments, ophthalmic inserts may be used for the controlled release of the ophthalmic estradiol formulations described herein. Ophthalmic inserts may be comprised of hydroxypropyl cellulose, such as the commercially available Lacrisert® (Aton Pharma. Inc.). Alternatively, ophthalmic inserts may comprise polyvinyl alcohol, as described in U.S. Pat. No. 4,730,013 (Bondi et al.).

In other embodiments, an ophthalmic gel carrier may be used for the controlled release of the ophthalmic formulations described herein. Ophthalmic gel carriers can provide good eye retention, can achieve sustained release, and are non-toxic. For example, the gel formulation described in U.S. Pat. No. 4,738,851 (Schoenwald et al.) may be used. The ophthalmic gel may be prepared using the combination of sodium carboxymethyl-cellulose and colloidal magnesium aluminum silicate, which avoids an initial burst release.

In yet other embodiments, a cationic emulsion may be used for the controlled release of the ophthalmic estradiol formulations described herein. For example, U.S. Pat. No. 6,656,460 (Benita et al.) describes a positively-charged submicron emulsion containing a phospholipid having Zeta potential values ranging from 34-45 mV and a mean droplet size of around 150-250 nm. The resultant electrostatic attraction between the positively-charged submicron oil droplets in the emulsion and the corneal eye surface, which is negatively-charged, results in a more prolonged residence or retention time conducive to topical drug flux enhancement. Similar ionic or non-ionic emulsions known in the art may also be used with the ophthalmic estradiol formulations described herein.

In an alternate embodiment, it is contemplated that sterile ophthalmic estradiol formulations described herein may be comprised of a liposomal drug delivery system whose aqueous phase comprises the pharmaceutical carrier of the present invention. Liposomal therapy has been successfully used in ophthalmology not only for pre- and postoperative antisepsis, but also for the treatment of bacterial and viral conjunctivitis and for prophylaxis against ophthalmia neonatorum. (Margalit R., *Liposome-Mediated Drug Targeting in Topical and Regional Therapies*, Crit. Rev. Ther. Drug Carrier Syst., 12(2-3):233-61 (1995)). A Method for formulating such a product can be found in U.S. Pat. No. 5,662, 931, which is herein incorporated by reference. Another example is DepoFoam® (Pacira Pharmaceuticals), which consists of multi-vesicular liposome particles that have numerous internal aqueous chambers that contain the encapsulated drug. The multi-vesicular liposome particles can release the encapsulated drug over a desired period of time, from 1 to 30 days.

In another embodiment, a capsule may be used for the controlled release of the ophthalmic estradiol formulations described herein. For example, a drug delivery system, such as that described in U.S. Pat. No. 7,204,995 (El-Sherif et al.) may be composed of a biodegradable biocompatible capsule (diameter of 0.01 mm to about 1 mm) associated with an estradiol formulation. The drug delivery system capsule would encapsulate the estradiol within a polymer shell or sphere. The capsules may be stored in the form of a powder that can be suspended in an aqueous carrier solution or dispersed in a gel or an ointment. The suspended capsules can be placed into the eye in the form of drops, and those dispersed in a gel or ointment can be placed in the eye in the form of a gel or ointment. The drug delivery system may work by slowly releasing the estradiol formulation into the eye through the polymer shell or sphere and/or gets secreted as the polymer degrades. Other examples of capsules that may control and maintain the release of the estradiol formulation include U.S. Pat. Nos. 4,853,224; 4,997,652; 5,164,188; 5,443,505; and 5,766,242 (Wong, et al.), and are hereby incorporated by reference.

In still another embodiment, hyaluronic acid or hyaluronate may be used as a viscosity enhancing agent to sustain the delivery of the ophthalmic estradiol formulations described herein. For example, U.S. Pat. No. 5,770,628 (Cantoro) discloses an ophthalmic preparation for use as an artificial tear comprising hyaluronate as a viscosity thickener, preferably in the form of an alkali salt and having a molecular weight of 500,000 to 4,000,000 Daltons, preferably about 1,200,000 to 1,400,000 Daltons, at a concentration that may range from 0.05 to 2% by weight, as well as comprising the following minimum quantities of ionic species: 40 mmol/l sodium ion, 12 mmol/l potassium ion, 0.4 mmol/l calcium ion, 0.4 mmol/l magnesium ion, 50 mmol/l chloride ion, 7 mmol/l phosphate ion and, preferably, 0.7 mmol/l citrate ion. The preceding size, concentration and quantities are merely for purposes of illustration without being limiting.

In another embodiment, minitablets may be used for the controlled release of the ophthalmic estradiol formulations described herein. For example, the PROLOC™ (Henkel AG & Co.) bioadhesive minitablets may be used. The PROLOC™ minitablets adhere to the ocular mucosa and remain in place until fully eroded. PROLOC™ achieves long lasting release and has high drug loading.

In still another embodiment, a cyclodextrin may be used for the controlled release by itself or in combination with other agents disclosed herein. For example, the cyclodextrin may be selected from α-cyclodextrin, β-cyclodextrin, or γ-cyclodextrin. Each of these three cyclodextrins has been Generally Recognized As Safe by the US FDA. Exemplary ranges for cyclodextrins include about 0.1% to about 10% (w/w), about 0.1% to about 7% (w/w), about 0.1% to about 1.0% (w/w) and about 0.6% (w/w).

In yet another embodiment, a biodegradable implant may be used for the controlled release of the ophthalmic estradiol formulations described herein. For example, the biodegradable implant may be formulated to provide a controlled, sustained drug release, as described in U.S. Pat. No. 7,048, 946 (Wong et al.). The release rate may be modulated by combining in the implant hydrophobic and hydrophilic agents. The rate of release of an estradiol formulation may be controlled by the rate of transport through a polymeric matrix of the implant, and the action of the modulator. By modulating the release rate, the estradiol formulation is released at a substantially constant rate, or within a therapeutic dosage range, over the desired period of time. The rate of release may not vary by more than about 100% over the desired period of time, preferably by not more than about 50%. The release modulator may act to accelerate or retard the rate of release. Accelerators may be physiologically inert, water soluble polymers, e.g. low molecular weight methyl cellulose or hydroxypropyl methyl cellulose (HPMC); sugars, e.g. monosaccharides such as fructose and glucose, disaccharides such as lactose, sucrose, or polysaccharides such as cellulose, amylose, dextran, etc. Alternatively, the accelerator may be a physiologically active agent, allowing for a combined therapeutic formulation. The choice of accelerator in such a case will be determined by the desired combination of therapeutic activities. Additionally, release retardants may be hydrophobic compounds which slow the rate of release of hydrophilic drugs, allowing for a more extended release profile, and may include non-water soluble polymers, e.g. high molecular weight methylcellulose and ethylcellulose, etc., low water soluble organic compounds, and pharmaceutically active hydrophobic agents.

It should be understood that the ophthalmic estradiol formulations described herein, for example 17-β-estradiol, may be used with any of the time-release or controlled release formulations described herein. In some embodiments the 17-β-estradiol concentration in solution may be present in amounts that range from 1%, 3%, or 5%, to 10%, 15%, or 20%. In other embodiments the 17-β-estradiol concentration in solution may be present in amounts ranging from 0.1%, 0.3%, or 0.5% to 1%, 3%, or 5%. In still other embodiments the 17-β-estradiol concentration in solution may be present in amounts ranging from 0.01%, 0.03%, or 0.05% to 0.1%, 0.3% or 0.5%. In preferred embodiments, the concentration of estrogen or estrogen analog or other estrogen receptor modulator, preferably 17-β-estradiol, is between about 0.005% and 5%, about 0.005% and about 0.1%, 0.005% and less than 0.05%, 0.01% and about 0.04%, about 0.05% and about 0.5%, about 0.05% and about 0.1%, about 0.1% and about 5%, or about 0.5% and about 5%, or is less than or equal to 0.1% weight-by-weight of estrogen or the estrogen analog or other estrogen receptor modulator.

Micro-Dose Delivery of Ophthalmic Estradiol Formulations

In addition to, or as alternative to, the time-release formulations, the ophthalmic estradiol formulations for topical administration to the conjunctiva, the inner eyelid or the outer eyelid described herein may be formulated for micro-dose delivery. Micro-dose formulations are another way to improve the concentration of estrogen delivered to the ocular tissues. Micro-dose formulations deliver a therapeutically effective dose of the estrogen or estrogen analogs or other estrogen receptor modulators disclosed in this specification in a lower volume than the standard ophthalmic drop, which therefore can include a higher concentration. The lower volume may be delivered by any means available to one of skill in the art. By way of example, a specialized micropipette that can deliver smaller than the standard ophthalmic drop may be used.

By way of example, the formulation disclosed in U.S. Pat. No. 6,096,733 of one drop of 0.1% 17-β-estradiol utilizes a standard ophthalmic drop (35 to 50 μl), so the dose is at least 35 micrograms of 17-β-estradiol. A preferred micro-dosing volume would be from 5 to 15 μl which could have a higher concentration while still delivering a lower overall dose of less than 35 micrograms. This lowered overall dose will have the effect of lowering the systemic effects of the drug and increasing adsorption. This method can be used with or without adding the necessary retention enhancing agents (the timed release/bioadhesive viscoelastic compounds) as discussed herein.

Ophthalmic Estradiol Formulations

This section sets out exemplary preferred formulations that may be used as starting points for formulation of the time-released forms disclosed herein. The exemplary starting formulations disclosed in this section are not limiting and one of skill in the art may readily begin with any preferred formulation when generating a timed release form a disclosed herein.

The preferred embodiments prior to formulation in a time-release form is as an aqueous solution of derivatives of estrogen known as 17-β-estradiol (or the 3-phosphate disodium salt) and its water-soluble, storage-stable derivatives (β-estradiol glucuronide β-estradiol hemisuccinate, β-estradiol phosphate, 3-estradiol sulfate and their 3,17 diesters, 17 monoesters and 3 monoesters) and/or one or more androgens, preferably selected from the group consisting of 17-α-methyl-17-β-hydroxy-2-oxa-5α-androstan-3-one, 4,5α-dihydrotestosterone derivatives, testosterone derivatives, 19-nortestosterone derivatives, 17β-hydroxy-5α-androstane derivatives containing ring A unsaturation, their esters, and their cationic or phosphorylated derivatives, designed to increase solubility in hydrophilic media. Particularly preferred androgens are 17-α-methyl-17-β-hydroxy-2-oxa-5α-androstan-3-one, 4,5α-dihydrotestosterone and phosphorylated derivatives. Particularly preferred pharmaceutically active substances for use with the pharmaceutical carrier of the present invention are those that are derivatized to have enhanced solubility and stability at essentially neutral pH 6-8 (though the pH is not absolutely critical and could suitably range between 4-8.5).

The formulation of 17-β-estradiol (as the 3-phosphate disodium salt) is $C_{18}H_{23}O_5P_1Na_2$, having a molecular weight of 396.3 (anhydrous). Each gram of 17-β-estradiol (as the 3-phosphate disodium salt) contains approximately 687 milligram of 17-β-estradiol on an anhydrous basis, 17-β-estradiol (as the 3-phosphate disodium salt) is available from Research Plus, Inc., Bayonne, N.J. 07002 (catalog No. 1850-5). The compound is a white crystalline powder with an ill-defined melting point and purity better than 98%. The material is to be stored in sealed vials under refrigeration when not in use.

In one embodiment, it is contemplated that a sterile, ophthalmic solution of 17-β-estradiol can be comprised of a liposomal drug delivery system (Margalit R., Crit. Rev. Ther. Drug Carrier Syst. 1995;12(2-3):233-61). Liposomal therapy has been successfully used in ophthalmology not only for pre- and postoperative antisepsis, but also for the treatment of bacterial and viral conjunctivitis and for prophylaxis against ophthalmia neonatorum (Reimer K, et al., Dermatology 1997;195 Suppl. 2:93-9). A Method for formulating such a product can be found in U.S. Pat. No. 5,662,931 (Munechika, K. et al.) and herein incorporated by reference. A liposome system for delivery of 17-β-estradiol is disclosed in example 3 below.

In an alternate embodiment, a sterile, ophthalmic suspension of 17-β-estradiol cypionate is dissolved to form a 0.1% (by volume) solution in a vehicle which may in one embodiment take the form of a lipid based solution having a pH within the range of 4-8 with a preferred range of about 6-8.

In another alternate embodiment, a sterile, ophthalmic solution of 17-β-estradiol (as 3-phosphate disodium salt) may be dissolved to form a 0.1% (by volume) solution in a vehicle which may in one embodiment take the form of a typical over-the-counter artificial tear solution. The concentration of 17-β-estradiol in the vehicle may be increased or decreased depending on the activity of the 17-β-estradiol (as 3-phosphate disodium salt). Below are alternate embodiments of the drops.

A. 17-β-estradiol (as the 3-phosphate disodium salt) and its water-soluble, storage-stable derivatives (beta-estradiol glucuronide, beta-estradiol hemisuccinate, beta-estradiol phosphate, beta-estradiol sulfate and their 3,17 diesters, 17 monoesters and 3 monoesters). The 17-β-estradiol 3-phosphate disodium salt may be employed in the preferred embodiment because of the enhanced solubility and stability of the particular derivative at essentially neutral pH 6-8 (though the pH is not absolutely critical and could have a pH between 4-8.5) and the ease of sterile ophthalmic manufacture.

TABLE 1

B. A sterile ophthalmic ointment formulated to melt at body temperature containing:

| Compound | Concentration (w/v %) |
|---|---|
| 17-β-estradiol (microcrystalline) | 0.05-0.1 |
| propyl paraben (USP) | 0.2 |
| anhydrous liquid lanolin | 5.0 |
| mineral oil (USP) | 10.0 |
| white petrolatum (USP) | 84.6-84.7 |

TABLE 2

C. A sterile aqueous ophthalmic suspension formulated to contain:

| Compound | Concentration (w/v %) |
|---|---|
| 17-β-estradiol (microcrystalline) | 0.05-0.1 |
| polysorbate 80 (USP) | 0.2 |
| povidone (USP) (K-30 type) | 1.0 |
| hydroxyethylcellulose (USP) | 0.5 |
| sodium chloride (USP) | 0.5 |
| disodium edate (USP) | 0.05 |
| benzalkonium chloride (USP) | 0.005 |
| dil. HCL for pH adjustment | qs |
| purified water (USP) | qs |

The following is a description of the manufacturing and packaging procedure for a preferred drug product of the invention. More information on the preparation and characteristics of poly-estradiol phosphate is set forth in the article by E. Diczfalusy entitled High Molecular Weight Enzyme Inhibitors, pp. 1675-1689, Chemica Scandinavia Vol. 12 (1958) No. 8, which is incorporated herein by reference.

The method of synthesis of 17-β-estradiol 3-phosphate disodium is reported in Acta Chem. Scan. 12, 1675-1689 (1958) and is briefly described as follows:

17-β-estradiol 17-acetate (Molecular Weight=314.4, Melting Point 220-224° C. and optical rotation 47°) may be phosphorylated in the presence of concentrated ortho-phosphoric acid ($H_3PO_4$) with heat and refluxing to yield the intermediate 17-β-estradiol 3-phosphate 17-acetate. The latter compound may be selectively hydrolyzed in the presence of sodium bicarbonate in aqueous alcohol to yield sodium acetate and 17-β-estradiol 3-phosphate disodium. The desired steroid phosphate ester may be recrystallized from dilute alcohol.

A complete list of components that can be present in a preferred embodiment of the drug product in accordance with the present invention—including the drug substance, is as follows (in percentages by volume):

17-β-estradiol (as 3-phosphate disodium salt) 0.1%

The concentration in subsequent batches may be increased or decreased depending upon the activity of 17-β-estradiol (as 3-phosphate disodium salt).

The vehicle may be supplied as a typical over-the-counter artificial tear (solution) with a composition of the vehicle as follows:

TABLE 3

| Compound | Concentration |
|---|---|
| povidone (USP) (K-30 type) | 1.67% by volume |
| hydroxyethylcellulose (USP) | 0.44% by volume |
| sodium chloride (USP) | 0.6% by volume |
| anhydrous sodium phosphate ($Na_2HPO_4$) (USP) | 0.3% by volume |
| disodium edate (USP) | 0.1% by volume |
| dil. HCL or NaOH for pH adjustment | qs |
| purified water (USP) | qs |

Based upon the chemistry of steroid phosphate esters, clarity of aqueous solution at essentially neutral pH values should be indicative of the presence of intact steroid phosphate ester. On the other hand, turbidity, haze formation or precipitate formation would indicate the presence of hydrolyzed, insoluble, free 17-β-estradiol.

Very small amounts of free, water-insoluble 17-β-estradiol can be tolerated in the steroid ophthalmic product as long as the homogeneity of the drug product is maintained because it is the 17-β-estradiol itself that is undergoing clinical study and not the phosphate ester pro-drug.

Solutions of drug product are preferably stored at controlled room temperature (15 to 30° C.) preferably at 22 to 24° C. as long as adequate physical stability (i.e., clarity of solution) is maintained. Otherwise storage under refrigeration (less than 10° C.) may be required.

It is also contemplated in an alternate embodiment, that the above drops may use a modified preservative system as described in Table 3. More particularly, this alternate embodiment can use methyl paraben at a concentration (w/v) of about 0.05-0.5% in combination with phenoxyethanol at a concentration (w/v) of about 0.1-1.0%.

The placebo that can be used in controlled clinical trials is the vehicle that can be used in the manufacture of the drug product, namely a typical over-the-counter artificial tear (solution), similar to the formula of which is identified previously. The placebo may be a non-prescription, over-the-counter drug product used to provide temporary relief of dry eye symptoms. It may contain mucin-like substances (povidone and hydroxyethylcellulose) which mimic the action of the conjunctival mucus or render the surface of the eye more wetable. The vehicle may help keep the eye moist and assures that the tear film can spread easily and evenly over the eye surface.

The preferred vehicle for 17-β-estradiol (as 3-phosphate disodium salt) may have the following attributes:
  a) a sterile, buffered isotonic or hypotonic solution.
  b) contains mucin-like substances that tend to increase the contact time between the active drug substance (17-β-estradiol (as the 3-phosphate disodium salt) and the eye surface.
  c) free of benzalkonium chloride, which is a cationic surfactant that is known to be incompatible in solutions with steroid sodium phosphate salts.

The following quality control procedures may be employed to assure identity, strength, quality and purity of the drug product:

Representative samples of finished drug product may be opened and examined for clarity of solution (clear, colorless to pale yellow solution, essentially free of foreign matter), pH content (not less than 4 and not more than 8.5) and a simple potency assay (absorbance read at 280 nanometers using 1 centimeter cells in a suitable spectrophotometer after diluting the drug product with alcohol or methanol to a suitable concentration.

In an alternate embodiment, it is contemplated that the composition of said invention may be free of any preservative compounds such as, for example, Thimerosal (USP) and said invention may be provided to patient in a sterile single or similar package allowing no more than 3 to 5 days of use before the patient discards the package.

In another alternate embodiment, it is contemplated that the present invention may utilize an ocular insert means of delivering the 17-β-estradiol ingredients directly to the ocular surface and conjunctiva. Such delivery systems are well known in the art and are exemplified by U.S. Pat. No. 4,478,818 (Shell et al.) of Alza Corporation (Palo Alto, Calif.) and hereby incorporated by reference.

In yet another alternate embodiment, it is contemplated that the present invention may utilize a thermosetting gel with a low sol-gel transition temperature as a method of delivering the 17-β-estradiol ingredients directly to the ocular surface and conjunctiva. Such a gel may be a clear physiologically acceptable solution at room temperature or lower but which forms a gel when placed in the eye exemplified by U.S. Pat. No. 4,474,571 (Haslam et al.) of Merck & Co., Inc. (Rahway, N.J.) and hereby incorporated by reference.

The quality control procedures are also the same as for the active drug product described above with the exception that the ultraviolet absorbance at 280 nanometers of the placebo solution when diluted to the same concentration as the active drug product will fail to indicate the presence of 17-β-estradiol (as the 3-phosphate disodium salt) in representative samples of the placebo solution.

Ophthalmic Androgen Formulations

Regarding the androgen that may be included with the estrogen or estrogen analog or other estrogen receptor modulator, selection of the most appropriate therapeutic androgen will depend upon a given hormone's immunological activity, potential side effects and form of administration. For example, topical testosterone may be quite effective in reducing ocular surface inflammation, and its methylated analogue appears to have no toxic side effects on parameters such as intraocular pressure (Knepper. P. A., Collins, J. A., and Frederick, R., *Effect of Dexamethasone, Progesterone, and Testosterone on IOP and GAGs in the Rabbit Eye*, Invest. Ophthalmol. Vis. Sci., 26:1093-1100 (1985)). However, a variety of other modified and/or anabolic androgens (Wilson, J. D., and Foster, D. W., eds., "Williams Textbook of Endocrinology," WB Saunders Company, Philadelphia (1985). Vida, J. A., "Androgens and Anabolic Agents," Academic Press, New York (1969)) may be more effective than testosterone.

In order to increase the aqueous solubility of the androgen, phoshorylated ester derivatives of the androgens are preferred and can be prepared by means commonly available in the art. For example, the most convenient method of synthesis of steroid esters is reaction of the steroid in a 2:1 mixture of pyridine and the anhydride of the desired ester: for example, propionic anhydride would be used to make the propionate ester. A large excess (at least 10 times) of the anhydride compared to the steroid would be required. This would then be purified by diluting with at least 10 parts of water to each part of pyridine, adding 1 part ether, decanting the water after shaking, and then washing with 10 parts water repeatedly in a separatory funnel. This would be followed preferably by recrystallization or chromatography for purification.

Androgens that may be used include testosterone, dihydrotestosterone (also termed allodihydrotestosterone, androstanolone, stanolone, 5 alpha-dihydrostesterone), fluoxymesterone, stanozolol, nortestosterone propionate, dehydroepiandrosterone (an androgen precursor, also termed androstenolone, dehydroisoandro-sterone, DHEA, transdehydroandrosterone), oxandrolone; methyldihydrotestosterone (also termed methylandrostanolone), oxymetholone, 5 alpha-androstan-17β-ol-3-oxime, 5 alpha-androstan-17 alpha-ol-3-one-acetate, (1) 2,(5 alpha)-androsten-17β-ol, 5 alpha-androstan-2 alpha-methyl-17β-ol-3-one, methyltestosterone, and their soluble ester derivatives.

These androgens are representative of the major structural subclasses of androgens, as disclosed in Vida (Vida, J. A., "Androgens and Anabolic Agents," Academic Press, New York (1969), hereby incorporated by reference. The subclasses include (a) androgenic compounds with unusual structural features (e.g., 17 alpha-methyl-17β-hydroxy-2-oxa-5 alpha-androstan-3-one, also termed oxandrolone); (b) testosterone derivatives (e.g., methyltestos-terone); (c) 4,5 alpha-dihydrotestosterone derivatives (oxymetholone); (d) 17β-hydroxy-5 alpha-androstane derivatives containing a ring A unsaturation, excluding testosterone derivatives (e.g., 2,(5 alpha)-androsten-17β-ol); and (e) 19-nortestosterone derivatives (e.g., 19-nortestosterone propionate). It may be that certain structural features impart more optimal immunosuppressive characteristics, which would be of benefit in selecting specific androgens for human use.

Also, relative to standards (typically testosterone), these androgens may include compounds displaying: (a) augmented androgenic (i.e., virilizing) activity coupled with an even larger increase in anabolic activity (e.g., fluoxymesterone); (b) enhanced anabolic action with unchanged androgenic effects (e.g., oxymetholone, dihydrotestosterone); (c) decreased androgenic ability with unchanged anabolic activity (e.g., 19-nortestosterone propionate); and (d) decreased androgenic capacity paralleled by increased anabolic activity (e.g., oxandrolone, stanozolol). Preferred androgens for use in compositions of the invention are those which have far more anabolic, than virilizing effect, (e.g., oxandrolone possesses 322% of the anabolic and 24% of the androgenic activity of methyltestosterone (Vida. J. A., "Androgens and Anabolic Agents," Academic Press, New York (1969)).

Additional Ophthalmic Carrier Formulations

This section sets out additional exemplary preferred formulations that may be used as starting points for formulation of the time-released forms disclosed herein. As above, the exemplary starting formulations disclosed in this section are not limiting and one of skill in the art may readily begin with any preferred formulation when generating a timed release form a disclosed herein. In some embodiments, the starting carrier composition prior to formulation in a time-release form or addition of the mucoadhesive viscoelastic compound may be an aqueous solution comprising, on a weight percent basis, about: Dibasic sodium phosphate, USP 0.05-1.0% Sodium Chloride. USP 0.2-0.9% Edetate disodium. USP 0.05-1.0% Povidone, USP 0.05-2.0% Poloxamer NF 0.001-0.05% Polyethylene glycol 0.05-1.0% Hydroxyethyl Cellulose NF 0.05-1.0% Purified water, USP, q.s to 100% HCl or NaOH to adjust pH to pH 6-8.

A more preferred starting composition of the invention may comprise: Dibasic sodium phosphate, USP 0.3% Sodium Chloride, USP 0.6% Edetate disodium, USP 0.1% Povidone. USP 0.37% Poloxamer NF 0.004% PEG 0.12% Hydroxyethyl Cellulose NF 0.2% Purified water. USP, q.s to 100% HCl or NaOH to adjust pH to pH 6-8.

The preferred Povidone can be K-15, or K-17, with K-17 being particularly preferred. The preferred Poloxamer can be Poloxamer 188. The preferred polyethylene glycol can be PEG 3350, and the preferred hydroxyethyl cellulose is Hydroxyethyl Cellulose 100.

The composition may optionally comprise one or more preservatives such as methylparaben, NF, and/or propylparaben, NF, and/or phenoxyethanol each of which may be present in an amount ranging from about 0.005 to about 0.5% by weight. The preferred composition can comprise both 0.04 weight percent methlyparaben and 0.02 weight percent propylparaben.

The foregoing ophthalmic carriers are merely for illustrative purposes without limiting the scope of the invention. One of skill in the art may readily utilize any other ophthalmically suitable carrier as long as the carrier is compatible with the estrogen or estrogen analog or other estrogen receptor modulator and with the time-release component(s) of the formulation.

The amount of active ingredient that can be admixed with the chosen carrier may depend on the use and factors such as the age of the patient, the particular condition to be treated, the frequency of administration, and the means of administration. The concentration of active ingredients can range from about 0.001 percent to about 10 percent by weight. In a most preferred embodiment, the concentration of 17-β-estradiol 3-phosphate disodium may be in the range of 0.01-1.0 weight percent. In another preferred embodiment, an androgen may be present in a concentration of about 0.001 to about 0.1 percent by weight of the composition.

The pharmaceutical carrier may itself be useful in alleviating symptoms of dry eye syndrome. As such it may be used by itself as a placebo, a tear substitute, or otherwise with or without the presence of active ingredients. The carrier, without the active ingredients, may also be useful in alleviating discomfort and minor irritation associated with the wearing of contact lenses.

EXAMPLE 1

Initial Dose Studies

Although the present invention has been described with reference to several illustrative examples, it will be understood that the invention is not limited to the examples given herein by way of illustration, but only by the scope of the appended claims.

Prior to an application of a drug formulated in accordance with the present invention it was necessary to establish the presence of dry eye syndrome in the test population and to follow its course under treatment. It is imperative that the diagnosis of dry eye syndrome be correct and the patient not be suffering from other or additional ophthalmic diseases such as Sjörgen's syndrome.

The diagnosis of dry eye syndrome in the present invention, was made on the basis of the following tests. Initially, microscopic evaluation of the tear film with particular attention to the marginal tear strip, viscosity and debris content of the precorneal tear film, and lid examination is performed. This is followed by staining the ocular surface with Rose Bengal, a vital dye which indicates cellular damage, Schirmer testing, tear osmolarity, measurement of tear break-up time (TBUT), and finally, the maturation index (a Papanicolaou stained sample of conjunctival epithelium) are then performed.

The diagnosis of menopause was confirmed with follicular stimulating hormone and luteinizing hormone serum determinants. Dry eye postmenopausal females had mean $E_2$ (estradiol levels) of 3.47 picograms/milliliter. Normal postmenopausal females had mean $E_2$ (estradiol levels) of 16.05 picograms/milliliter (U.S. Pat. No. Re. 34,578, col. 2, Ln. 56-59).

A non-time release topical drug product comprised a sterile solution of estradiol cypionate dissolved in a lipid (oil-based) vehicle at a concentration of 0.05 milligram/milliliter was tested for its effectiveness as a therapy for postmenopausal, dry-eye syndrome in a controlled, double-blind study. The non-time release topical drug product was tested to determine dose response. As a pilot project, the dose was changed after one week to 0.1 milligram/milliliter, and after two weeks to 1.0 milligram/milliliter, all performed as medication in one eye and placebo (medium) in the other.

Two drops given three times a day were indicated, but it was found that application may be more or less frequent. However, it was determined that other alternative pharmaceutical modes of administration may be used—such as a slow release mode, or any other topical method, and that the concentration may vary with individual response, as well as the treatment intervals and duration. Blood levels of the hormone used were also determined. A control bottle of just the aqueous vehicle was also made, using the estrogen preparation for one eye of the patient and the control vehicle for the other eye. A dosage of the drops four times a day for several weeks, during which time osmolarity and maturation indices were performed. No change was noted in the maturation index or osmolarity, thus the concentration was increased to (0.05%). After ten days of treatment, the control eye showed no change in the experimental parameters while the eye receiving topical estrogen showed epithelial maturation commonly seen during ovulation in premenopausal females.

The effectiveness of estrogen and its derivatives in treating keratoconjunctivitis sicca was confirmed by the use of an intravenous sterile solution of conjugated estrogens kept refrigerated during use. The drug remained active for 60 days when refrigerated at 4-15° C.

Blood Concentrations of Estrogen in Subjects Treated with 0.1% 17-β-estradiol were measured. The measurements fell within a range 0 to 30 milli-International Units (m I.U.) of 17-β-estradiol.

TABLE 4

| Estrogen Blood Level at 0.1% dose | |
|---|---|
| Patient No. | Estrogen Blood Level at 0.1% dose |
| 1 | 13 |
| 2 | 36 |
| 3 | 136 |
| 4 | 3 |
| 5 | 9 |
| 6 | 40 |
| 7 | 19 |
| 8 | 89 |
| 9 | 12 |
| 10 | 22 |
| 11 | 41 |
| 12 | 44 |

The average blood concentration of estrogen in test subjects was 15.5 m I.U. The average blood concentration of estrogen in the placebo group was 0.99 m I.U. at the beginning of the study and 7.34 m I.U. at the end of the study.

EXAMPLE 2

Results of Clinical Trials Using 17-β-estradiol to Teat Dry Eye

A phase 1 human clinical trial was conducted between November 1993 and December 1995. The objective of the present study was to evaluate the efficacy and safety of a non-time release formulation of 17-β-estradiol in relieving the signs and symptoms of dry eye syndrome in postmenopausal women. 45 completed subjects were studied in the single-center, randomized, double-masked, parallel, placebo controlled study. The trial was conducted as follows:

The initial visit (Visit 1) occurred 7 days prior to the actual start of the study, where subjects were screened. Information regarding health, ophthalmic history, and patient evaluation and inclusion/exclusion based on FDA approved criteria were performed. A complete ophthalmic examination which included:

Acuity testing
Biomicroscopy
Intraocular pressure (IOP)
Ophthalmoscopy
Color vision
Tear osmolarity
Schimer's test
Tear film break-up time (TBUT)
Superficial punctate keratitis (SPK)
Rose bengal staining (RBS)

In addition, blood was drawn for FSH, LH and estradiol levels and a urine sample was collected for pregnancy testing where necessary. Subjects were given the placebo vehicle and instructed to instill the drops four times a day in both eyes for seven days. Daily diaries were provided and subjects were given instructions on using them. They were also instructed to discontinue use 12 hours prior to the next visit and to do the same before subsequent visits.

On Visit 2 (Day 1 of the study) the patient's medical history was updated and all symptoms of ocular discomfort were evaluated and recorded. The same measurements were taken as in Visit 1. All those which qualified were randomized and received 0.1% estradiol, 0.25% estradiol or placebo.

The first drop of the assigned study drug or placebo was instilled in the eyes of each subject at the investigator's office. Signs or symptoms of dry eye were then evaluated by the investigator at 15, 30, and 60 minutes post-instillation. Subjects were then instructed to begin instilling the drug four times a day for a total of 90 days beginning the next day. Signs and symptoms of dry eye were evaluated by subjects immediately before the 8:00 a.m. (first) dosage and 8:00 p.m. (last) dosage of the drops.

The subjects returned for follow-up on days 14, 30, and 60. During these visits the patient's medical history was updated and all symptoms of ocular discomfort were evaluated and recorded. The same measurements were taken as in Visit 2.

On the final exit visit (Visit 6), the subjects stopped the treatment regimen and reverted back to their usual ocular lubricants. The same examination procedures were performed as on Visit 1. All study drugs and subject daily diaries were collected and an exit form for each patient was completed for all subjects. All subjects were advised to return for a post-study follow-up on day 105 (Visit 7), with the same examination procedures were performed as on Visit 1.

The results of the study were most impressive. The data indicated a strong trend that estradiol drops significantly improve both hallmark symptoms and objective parameters. Graphical representations of the mean change for subjective scores, SPK, Rose Bengal, TBUT, and Osmolarity are shown in FIGS. 1 to 5, respectively. Statistically significant results were found when evaluating subjective complaints of redness and foreign body sensation amongst placebo and treatment groups. When comparing the two treatment groups combined vs. placebo, the p-values for tear break up time were 0.08 and for the subjective measures, the p-value was 0.13. When the 0.1% group was independently compared to placebo, the p-value for osmolarity came to 0.056 and for tear break up time 0.066.

Forty four of forty five patients completed the entire study. Although the study size is limited (due to severe inclusion/exclusion criteria) and provides us with only a 40% chance of finding a moderate to large clinical effect at a p=0.05, several findings stand out. If one looks at the means of the differences for all groups (placebo, 0.1% Estradiol, 0.25% Estradiol), the mean difference in the score between the second and sixth visits (T6–T2) for all subjective (FIG. 1) and objective outcome' variables), several of the measures (tear break up time (FIG. 4), Rose Bengal (FIG. 3), Osmolarity (FIG. 5), the sum of the subjective measures) deviate in the hypothesized direction. For example, the means for tear break up time decrease with increasing dosage. The second and sixth visits were used because the study medication was started on visit 2 and stopped at visit 6.

A Wilcoxon Rank Sum Test on the 0.1% group was independently compared with the placebo group on all clinical and subjective measures (table 5). As this data was normally distributed, t-tests were used to assess if the means of the variables differed.

TABLE 5

Analysis Of Mean Difference Between Placebo And 0.10% Estradiol Treatment

| Test | N value | P-value |
|---|---|---|
| Osmolarity | | 0.056 |
| Placebo | 12 | |
| 0.10% | 18 | |
| TBUT | | 0.066 |
| Placebo | 12 | |
| 0.10% | 18 | |
| Subjective | | 0.17 |
| Placebo | 12 | |
| 0.10% | 18 | |
| Rose Bengal | | 0.17 |
| Placebo | 12 | |
| 0.10% | 18 | |
| SPK | | 0.72 |
| Placebo | 12 | |
| 0.10% | 18 | |
| Schirmer's | | 0.82 |
| Placebo | 12 | |
| 0.10% | 18 | |

Finally, an analysis of the individual subjective ratings was performed (FIG. 1). Three tests were conducted. First, an overall test looked for differences in the distribution of scores among the three groups without regard to level. Differences between the 0.1% group and the placebo group were then tested (Table 6). Two ratings emerged as significant at a p-level of less than 0.05: foreign body sensation and redness. For both ratings, the treatment groups showed significantly more improvement than the placebo group.

TABLE 6

Analysis of Subjective Scores of
Placebo v. 0.10% Estradiol

| Test | Wilcoxon values |
|---|---|
| FBS | 0.044* |
| Redness | 0.013* |
| Itching | 0.20 |
| Burning | 0.85 |

*indicates that the results were statistically significant

The FDA found that the results of the study succeeded in its purpose in demonstrating the effectiveness of estrogen eye drops in the postmenopausal dry eye and approved advancing the study to a phase 3 trial involving two formal clinical trials in two separate centers using the final formulation.

A small Phase IIb trial was conducted to compare the 0.1% formulation with a 0.05% formulation to see if a lower dose could be used to obtain similar results while lowering the systemic estradiol levels as indicated on Table 4. The Target Patient Population (TPP) group was defined as those patients enrolled who presented with an AST score of <7 mm/5 minutes and an LGS-Conjunctiva (nasal+temporal) score of >2 (≥3) in the Signal Eye on Day 0. The TPP was the patient group with moderate-to-severe Dry Eye that will likely be selected for the Phase III trial. As opposed to the ITT (Intent-to-Treat) group which comprises all enrolled patients, the TPP was a subgroup that comprises about half (15/30 in the 0.1% group) of the ITT, and which demonstrated the most benefit in the main signs (AST (Anesthetized Schirmer's Test—a test for the volume of tears produced in 5 minutes); LGS-cornea (Lissamine Green Staining—a test for damage to the cornea and conjunctival surface); and SPK (Superficial Punctate Keratitis—similar to LGS but using a different dye)) and symptom (FBS (Foreign Body Sensation—typical symptom in dry eye found in many patients)).

Figure 6:
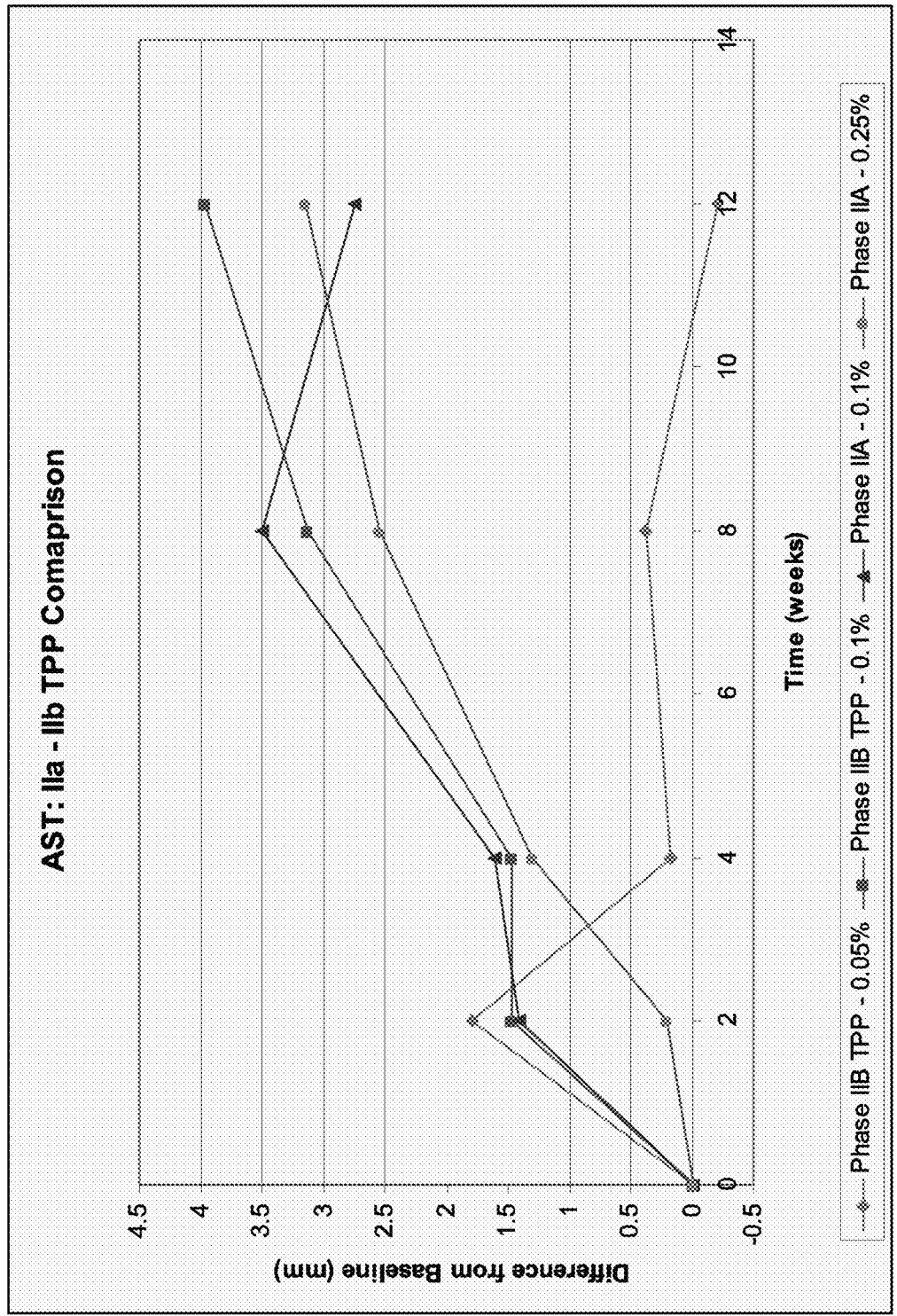
FIG. 6 shows a graph of the AST averaged for both eyes over time for the concentrations of non-time release formulations tested in the Phase IIa (0.1% and 0.25%) and Phase IIb (0.1% and 0.05%) trials.
Figure 7:
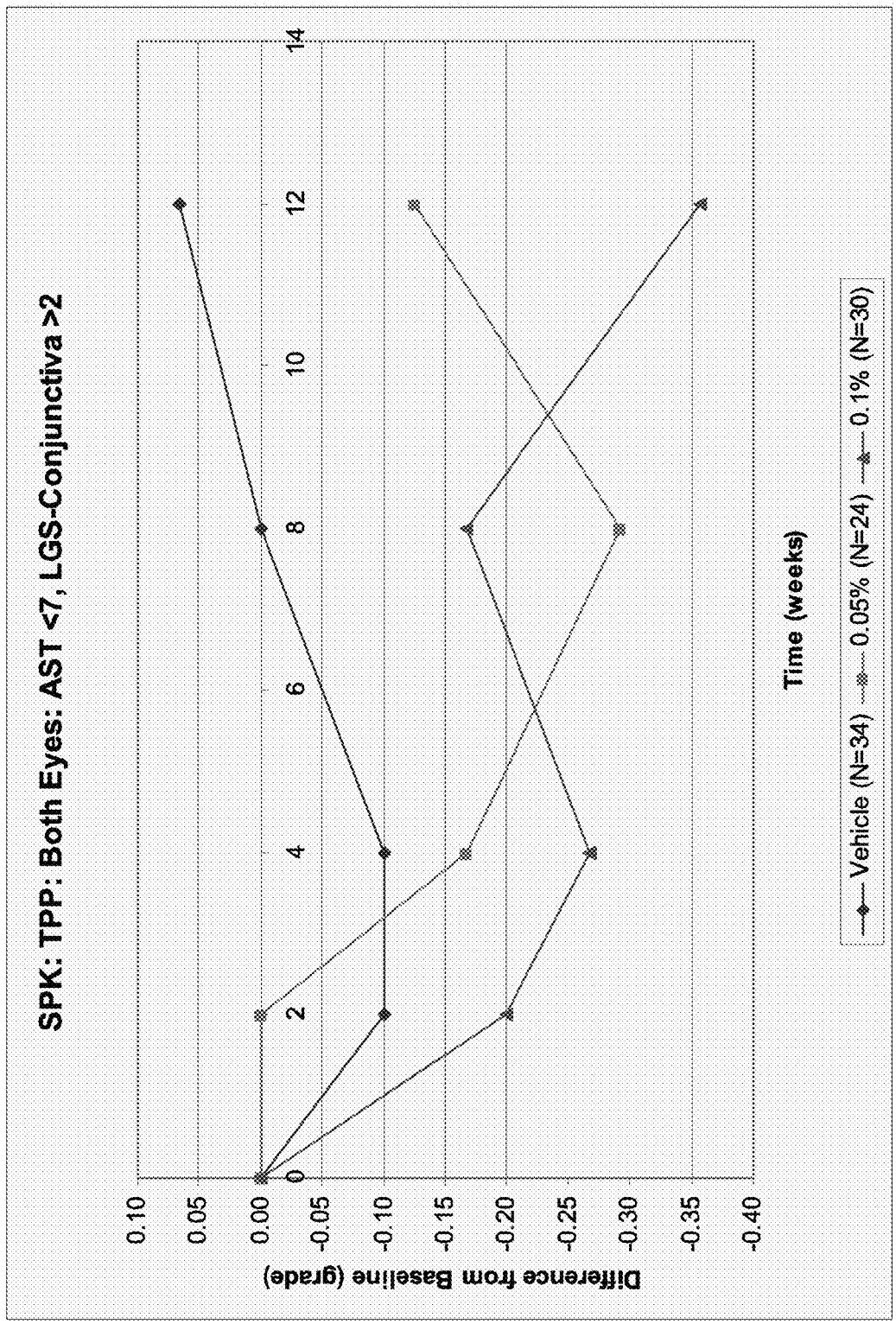
FIG. 7 shows a graph of the SPK averaged for both eyes over time for the two concentrations of non-time release formulations tested in the Phase IIb (0.1% and 0.05%) trial.
Figure 8:
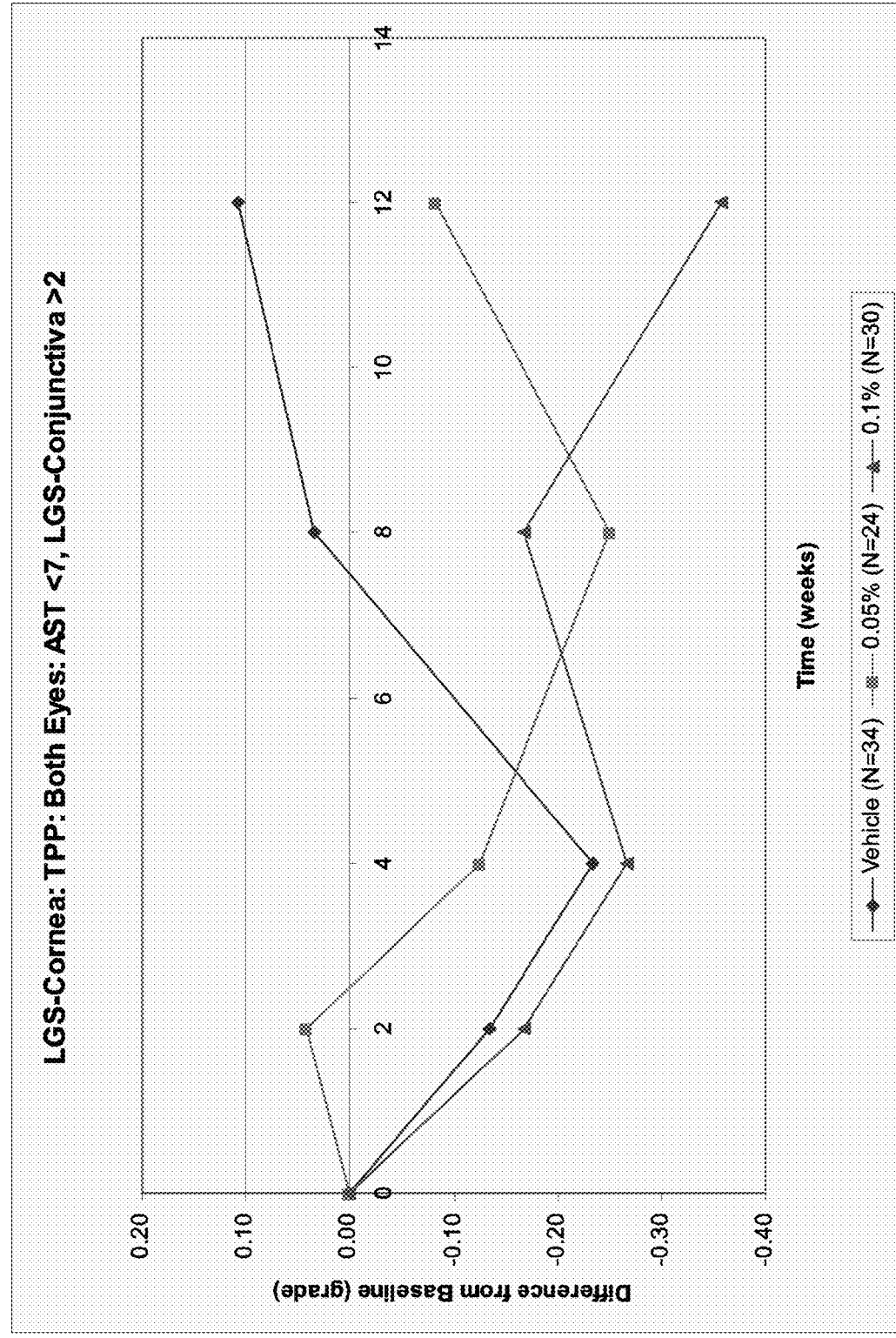
FIG. 8 shows a graph of the LGS-cornea averaged for both eyes over time for the two concentrations of non-time release formulations tested in the Phase IIb (0.1% and 0.05%) trial.
Figure 9:
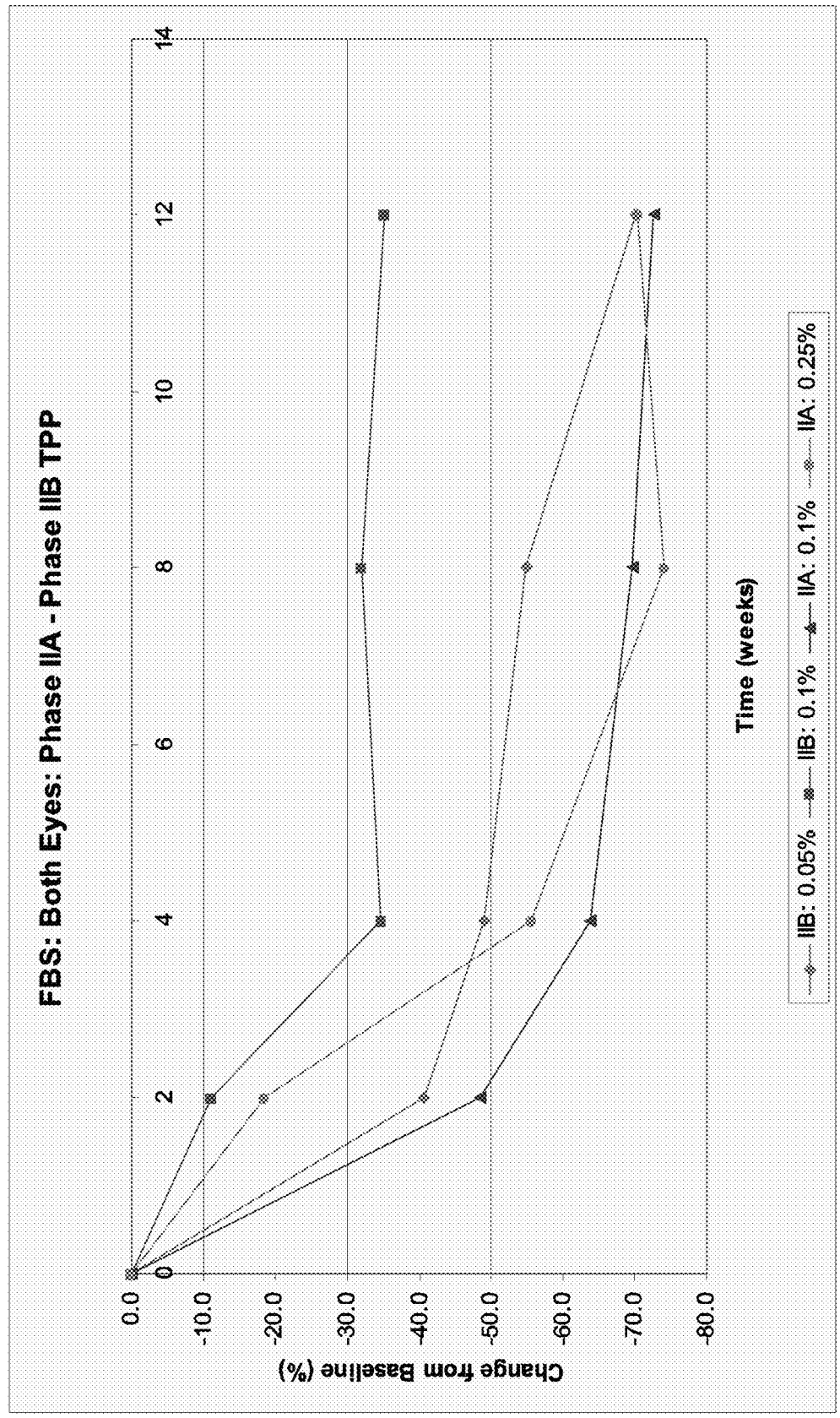
FIG. 9 shows a graph of the AST FBS for both eyes over time for the concentrations of non-time release formulations tested in the Phase IIa (0.1% and 0.25%) and Phase IIb (0.1% and 0.05%) trials.

The results for the Phase IIb trial showed that the lower concentration was generally less efficacious that the 0.1% formulation. For AST, the 0.1% formulation was clearly superior to the 0.05% formulation and the vehicle alone, which produced similar results. See FIG. 6. This applied for study eye alone and both eyes averaged data. For SPK, the 0.1% formulation was superior to the vehicle alone (though not statistically significant in single eye evaluation presumably due to small sample size and variability of individual data points but statistically significant when both eyes averaged), and the effect was numerically better than the 0.05% formulation and occurred earlier. See FIG. 7. For LGS, the trend observed favored the 0.1% formulation over the vehicle alone. See FIG. 8. For the FBS, an unexpected reversal for the symptom was observed where the 0.05% formulation outperformed the 0.1% formulation. The most likely explanation was a combination of the symptoms being subjective and therefore subject to a wider variability and the small group size. FIG. 9 shows combined results from the Phase IIa and Phase IIb trials. From the figure, it is clear that the patients receiving the 0.1% formulation in the Phase IIb reported an unusually low response. The patients receiving the 0.1% formulation in the Phase IIa reported a similar response as the patients receiving the 0.05% formulation in the Phase IIb trial.

The overall picture leads to the conclusion that despite the result for FBS, the 0.1% aqueous formulation is the better dose to take to Phase III if the formulation were to remain unchanged. The FBS result was the only one that favored the 0.05% formulation, which may have been due to the small population size or the subjective nature of the test.

EXAMPLE 3

Formulation of Time-Release Topical Application Pharmaceutical

Various pharmaceutical compositions will be formulated based upon the following starting composition:

TABLE 8

| Compound | Concentration (w/v %) |
|---|---|
| 17-β-estradiol (microcrystalline) | Desired amount |
| polysorbate 80 (USP) | 0.2 |
| povidone (USP) (K-30 type) | 1.0 |
| hydroxyethylcellulose (USP) | 0.5 |
| sodium chloride (USP) | 0.5 |
| disodium edate (USP) | 0.05 |
| benzalkonium chloride (USP) | 0.005 |
| dil. HCL for pH adjustment | qs |
| purified water (USP) | qs |

The formulations will not include any preservative. The following bioadhesive viscoelastic compounds will be added each in its own formulation: Sodium Hyaluronate (0.05% to 0.2%), xanthan gum, hydroxypropyl methyl cellulose (0.5% to 2.0%) and polycarbophil. After addition of the bioadhesive viscoelastic compound has been added, the excipients will be adjusted to maintain isotonicity of the formulation. After adjustment of the isotonicity, the formulations will be subject to basic diffusion studies to verify adequate delivery of the 17-β-estradiol. The concentration of the 17-β-estradiol and/or the amount of bioadhesive viscoelastic will be adjusted such that the appropriate concentration of 17-β-estradiol is delivered. The final formulations will then be subject to accelerated stability studies for one month at 55° C., 40° C. and 25° C.

EXAMPLE 4

In Vitro Erosion Diffusion Model

After formulations for multiple time-release topical applications pharmaceutical have been finalized as per Example 3, the time-release formulations will be tested in an erosion/diffusion model. Samples will be pulled from the receiver chamber at selected time points. Samples will also be pulled from the outflow of the upper/donor chamber at the same time points. The samples will be stored and tested by for Estradiol.

EXAMPLE 5

In Vivo Testing

The preferred formulation identified in Example 4 (or in Example 7) will be made using radiolabeled estradiol for preclinical in vivo animal testing. Various treatment levels of estradiol for the formulation(s) will be dosed for 7 days at various dosing regimens times per day followed by a radiolabeled treatment on day 8. Samples collected at various intervals post-dose of radiolabel.

The plasma, tear, and tissues samples will be tested by liquid scintillation counting to assess recovery of 3H-estradiol in the samples and provide time-concentration data.

Thus, there will be an adequate number of rabbits for samples at each time point for each treated group. The three untreated animals will be collected amongst the treated groups as a check for cross contamination. Total tear weight will be collected. Additional ocular tissue samples and blood samples will be collected. All tissue samples will be stored on dry ice and then at −80° C. until analysis. All blood samples will be drawn with EDTA coated syringes. Blood samples will be appropriately stored to retain integrity prior to analysis.

EXAMPLE 6

Clinical Trial of Timed Release Formulations

The overall design of the phase II clinical trial to test the efficacy of the optimal formulation determined from Example 5 is as follows. An initial patient pool of 105 patients will be screened. After a run-in period, patients will be randomized to receive one of the test products or their vehicle. The new formulation will be tested when used as a once nightly or twice daily application. Table 9 contains additional details of the phase II clinical trial.

TABLE 9

| | |
|---|---|
| Title | iDESTRIN ™ New Timed Release Formulation (iDNF) vs placebo |
| Protocol Number | ALT-001v1 |
| Development Phase | II |
| Primary Objectives | 1) iDNF Conc. X % vs iDNF Conc. 2X % vs. iDNF placebo<br>   i) used ONCE at night and ii) used TWICE daily.<br>2) Local Tolerance and systemic safety of both iDNF concentrations.<br>3) Systemic estradiol levels at both concentrations and dose regimens. |
| Secondary Objective | 1) Comparison between o.n. and b.d. dose regimens<br>2) |
| Study Design | Double masked, parallel group, 3-arm, placebo controlled randomized study with a run-in period. |
| Number of Subjects | (3 × 30) + 15 reserve = 105 patients. |
| Number of Centers | 6 sites |
| #pt/site | 17 |
| Inclusion Criteria | Post menopausal females NOT using HRT with moderate to severe dry eye disease. |
| Exclusion Criteria | To be defined |
| Duration of study/pt | 15 weeks |
| # visits/pt | 8 (Screening + 7 visits) |
| Test product | iDNF Concentration X<br>iDNF Concentration 2X |
| Comparator | iDNF vehicle |
| Primary Endpoints | Symptoms: OSDI/DEQ<br>Signs: Staining (Oxford Scale) |
| Secondary Endpoints | Individual symptoms including ocular discomfort, dryness, foreign body sensation, irritation, etc.<br>Signs including Schirmer's test, TBUT, Lissamine green staining, tear osmolarity, etc. |

EXAMPLE 7

Franz Diffusion Cell Model

A Franz diffusion cell model was modified to include simulated tear flow to better assess the impact of formulation changes on the diffusion of active moieties across isolated rabbit corneas. The methodology has previously been described (Rowe T E et al., Measurement and Prediction of Timolol Diffusion with and Without Simulated Tear Flow, Association for Research in Vision and Ophthalmology Congress, May 2010, Poster 2452.). To test this model, an in vitro trans-corneal diffusion study comparing Timoptic (solution) and Timoptic XE (gel) was performed under both static and simulated tear flow conditions. The amount of Timolol that diffused across the cornea as well as the amount of Timolol retained in the pre-corneal (donor) area were compared. The Franz diffusion cell model without simulated tears showed no difference between Timoptic (solution) and Timoptic XE (gel). By contrast, the results from the Franz diffusion with simulated tears were comparable to those published in vivo data for the two products (Burgalassi et. al. (2000) Xyloglucan as a Novel Vehicle for Timolol: Pharmacokinetics and Pressure Lowering Activity in Rabbits, *J. Ocular Pharm. Therapeutics*, 16(6): 497-509.). Therefore, the Franz diffusion model with simulated tears used in this Example 7 provides an accurate model of the delivery of active ingredients in vivo.

Formulations

In all experiments in this Example 7, the aqueous portion of the formulation was the same as the formulation used in the phase IIb study discussed in Example 2 above. The aqueous formulation containing 0.1% 17-β-estradiol phosphate was used as control. Test formulations varied in 17-β-estradiol free acid concentration and excipients and include:

1. Standard formulation (0.078% 17-β-estradiol free acid)
2. 0.034% 17-β-estradiol in carbopol 980 (2% w/w)
3. 0.025% 17-β-estradiol in carbopol 980 (2% w/w) and hydroxy propyl beta cyclodextrin (CD) (0.4% w/w)
4. 0.017% 17-β-estradiol in Xanthan gum (0.6% w/w)
5. 0.016% 17-β-estradiol in Xanthan gum (0.6% w/w) with CD (0.4% w/w)

Results

The data was obtained by performing three studies. The formulations compared in each of the three studies were as follows:

Study 1 was a comparison of the following formulations for 180 minutes:
    Standard formulation (the formulation used in the Phase IIb studies which contains 0.078% 17-β-estradiol phosphate)
    0.034% 17-β-estradiol in carbopol
    0.025% 17-β-estradiol in carbopol and cyclodextrin (CD)

Study 2 was a comparison of the following formulations for 180 minutes:
    Standard formulation (the formulation used in the Phase IIb studies which contains 0.078% 17-β-estradiol phosphate)
    0.017% 17-β-estradiol in Xanthan gum
    0.016% 17-β-estradiol in Xanthan gum with CD Study 3 was a comparison of the following formulations for 360 minutes:
    Standard formulation (the formulation used in the Phase IIb studies which contains 0.078% 17-β-estradiol phosphate)
    0.016% 17-β-estradiol in Xanthan gum with and cyclodextrin (CD)
    0.034% 17-β-estradiol in carbopol Results—Objective #1

The first objective was to improve the overall availability of 17-β-estradiol to ocular surface tissues by increasing the duration of the drug on the ocular surface. In other words, allowing the active ingredient to be present on the ocular surface for a longer period of time.

Figure 10:
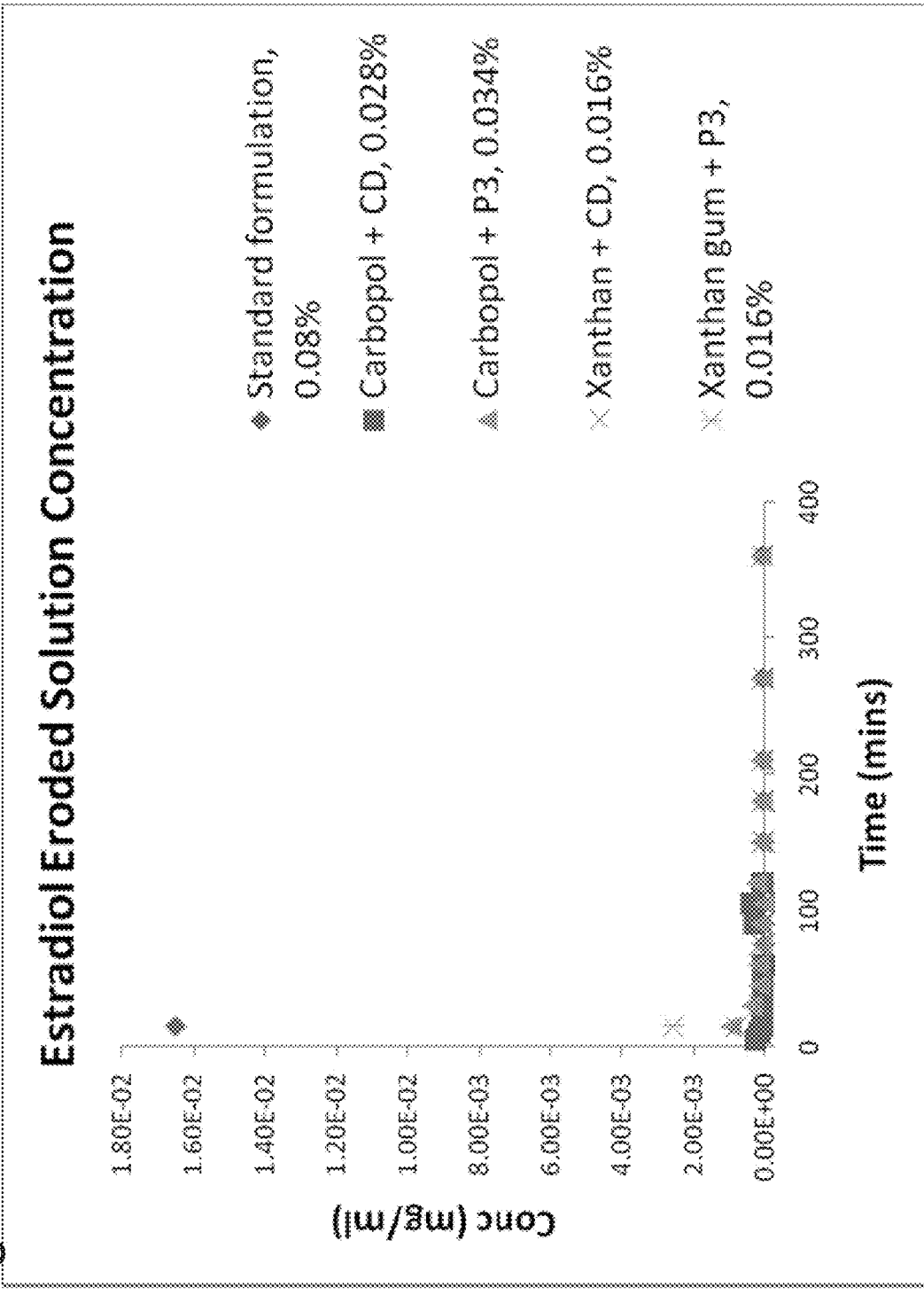
FIG. 10 shows a graph of the estradiol eroded solution concentration over time for the standard formulation (aqueous) and for four novel timed release formulations.

The impact of the formulation on this parameter was best exhibited by the concentration profile exhibited in the erosion data. Overall, the data indicated that delivery of the aqueous (Phase IIb—0.1% 17-β-estradiol) formulation to the simulated ocular surface results in a surge of 17-β-estradiol which is rapidly depleted after the first fifteen minute time interval. The timed release formulations have a more limited early release profile and maintain a higher concentration on the surface of the eye until about the 180 minute mark. FIG. 10 is a plot of the erosion concentration data.

The standard 0.1% aqueous formulation demonstrated a typical pattern of solution erosion with 74% of the erosion occurring within the first 15 minutes. This corresponds well with the recorded peak blood concentration of estradiol recorded in clinical trials with iDESTRIN discussed in Example 2 above, which occurred at twenty minutes post instillation.

Of the novel formulations, only the Xanthan gum P3 formulation, with a corresponding value of 54%, showed similar rapid erosion in the immediate period post instillation. This formulation appears to mirror the performance of the standard throughout the observation period.

Figure 11:
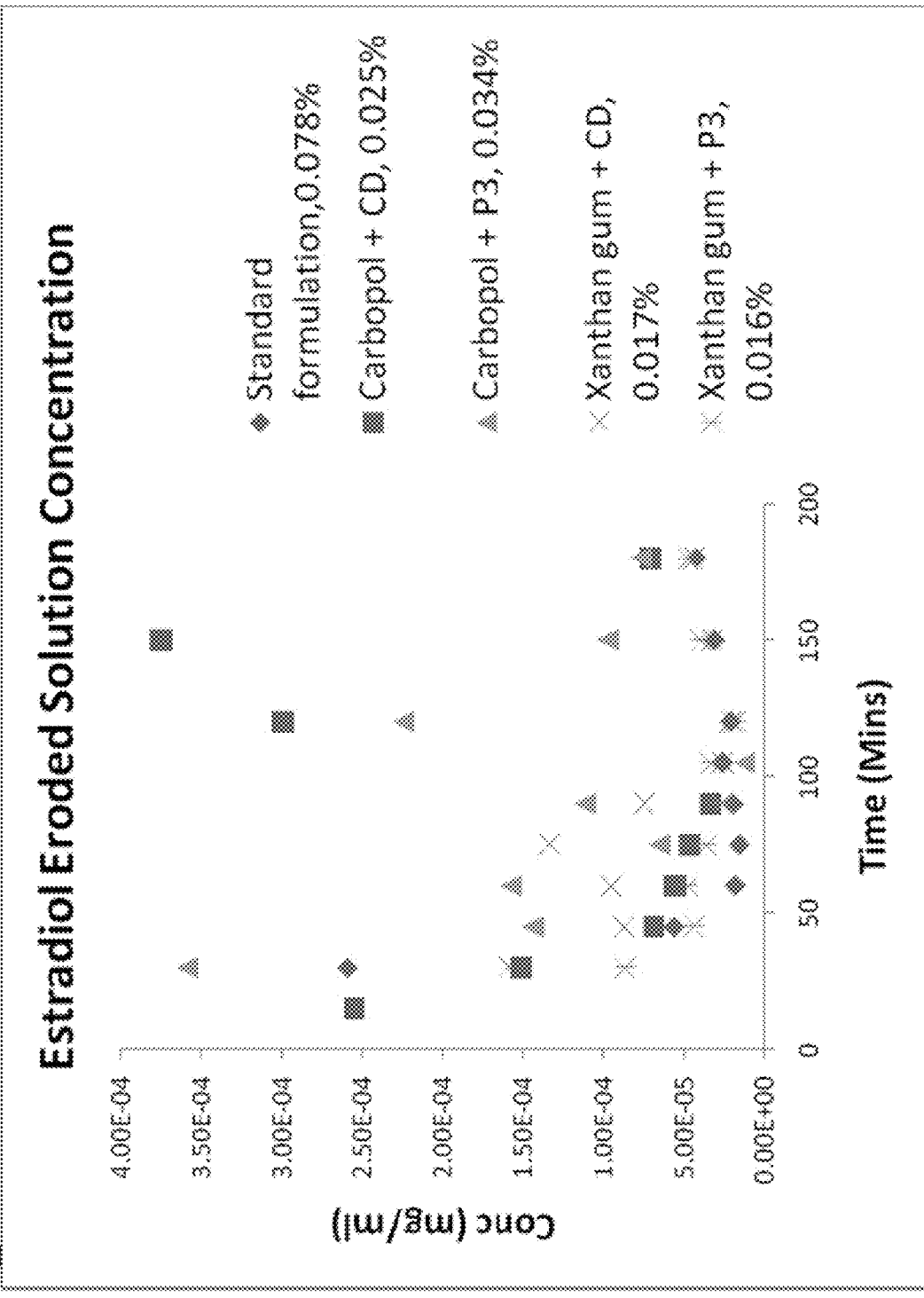
FIG. 11 shows a second graph of the estradiol eroded solution concentration over time for the standard formulation (aqueous) and for four novel timed release formulations with values on the y-axis capped at 2.00E-03 to better show differences at lower concentrations.

Due to the considerable drop in the 17-β-estradiol concentration from the initial data for the standard and the xanthan P3 formulation, it is not possible to display the changes over time with the other formulations on FIG. 10. FIG. 11 applies a limit on the upper range of the y axis concentration value to 0.0005 mg/ml in order to have an improved review of the differences in concentrations of the different formulations over a more prolonged time (30 min to 180 min). This extended time in estradiol erosion concentration is expected to result in improved adsorption of the drug by ocular surface tissues.

The key formulation improvements here were observed with the CP3 (Carbopol gel formulation) and the Xanthan+CD formulation.

Overall the data indicated that a much higher concentration of 17-β-estradiol was delivered by the phase IIb aqueous formulation in the early stages of delivery. The middle stages of delivery (30 to 180 minutes) show a "maintenance" level that is significantly different when comparing the aqueous formulation (0.0.08%) to the timed release formulations including Carbopol+P3 formulation (0.034%) and the Xanthan+CD formulation (0.16%). This data is also represented in Table 10 below. In general, the data indicated the following:

The aqueous formulation and the Xanthan P3 formulation had similar erosion profiles.
The timed release Carbopol CD formulation showed an unexpected profile as it increased over time. This may be an artifact of the combined release profile of the drug diffusing out of the CD into the gel matrix and out of the matrix into the simulated tear film.
The timed release Xanthan CD formulation had a higher concentration than the aqueous formulation. This advantage disappeared after 3 hours which is probably an indication that the xanthan had eroded away and no longer provided a reservoir for the drug.
The timed release Carbopol P3 formulation appeared to give the best results with a huge difference in concentration even after 6 hours.

TABLE 10

Eroded Solution concentration (mg/mL)

| Time (mins) | 2B (STD) | CP3 | C-CD | X CD | X P3 |
|---|---|---|---|---|---|
| 15 | 0.01652 | 0.00095 | 0.00026 | 0.00080 | 0.00258 |
| 30 | 0.00026 | 0.00036 | 0.00015 | 0.00016 | 0.00009 |
| 45 | 0.00006 | 0.00014 | 0.00007 | 0.00009 | 0.00004 |
| 60 | 0.00002 | 0.00016 | 0.00006 | 0.00010 | 0.00005 |
| 75 | 0.00002 | 0.00007 | 0.00005 | 0.00013 | 0.00004 |
| 90 | 0.00002 | 0.00011 | 0.00003 | 0.00008 | 0.00003 |
| 105 | 0.00003 | 0.00001 | | 0.00003 | 0.00003 |
| 120 | 0.00002 | 0.00022 | 0.00030 | 0.00002 | 0.00002 |
| 150 | 0.00003 | 0.00010 | 0.00038 | 0.00003 | 0.00004 |
| 180 | 0.00004 | 0.00008 | 0.00007 | 0.00004 | 0.00005 |
| 210 | 0.00005 | 0.00010 | | 0.00004 | |
| 240 | | | | | |
| 270 | 0.00007 | 0.00006 | | 0.00005 | |
| 300 | | | | | |
| 330 | | | | | |
| 360 | 0.00008 | 0.00009 | | 0.00007 | |

Results—Objective #2

Figure 12:
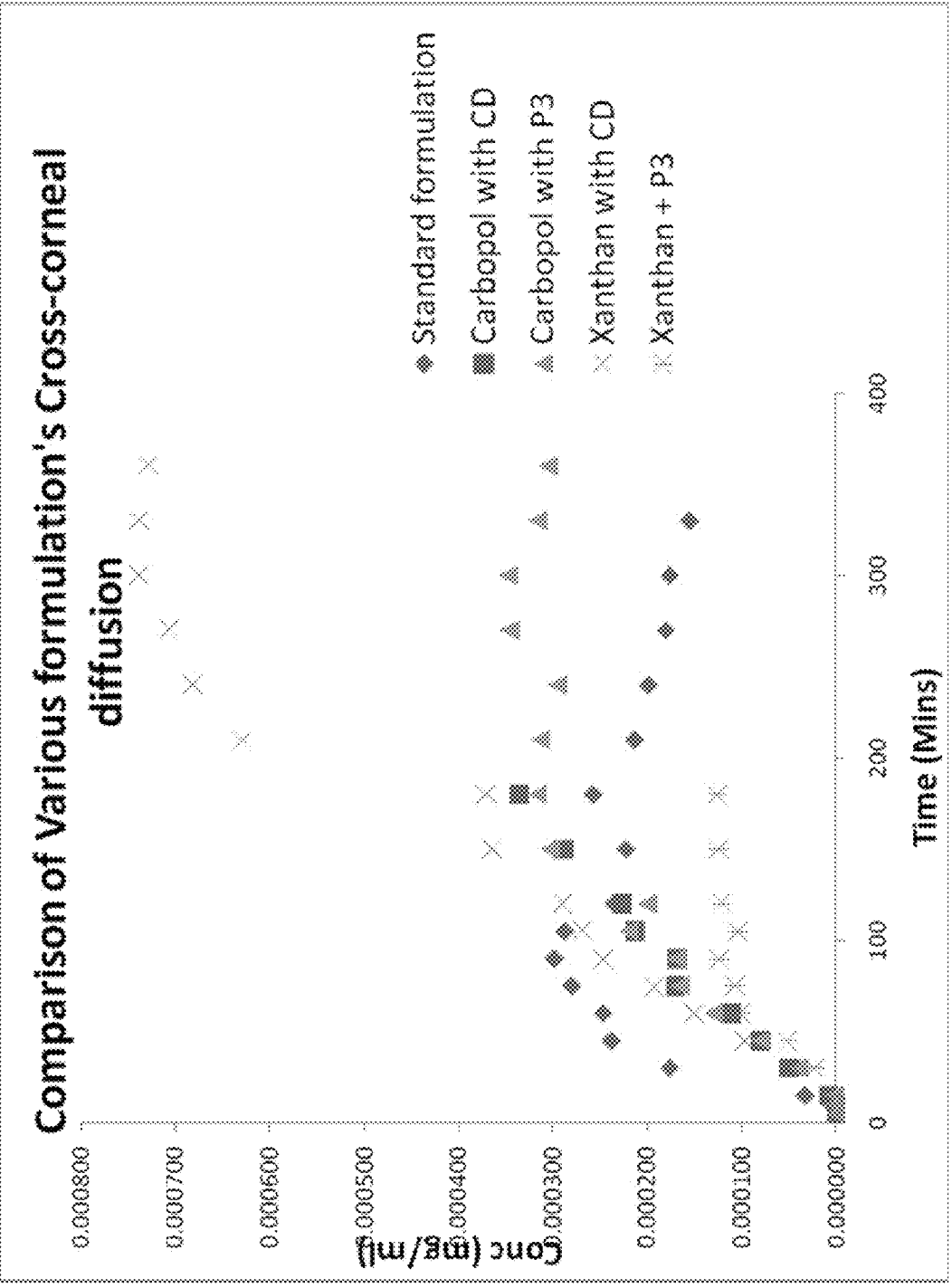
FIG. 12 shows a graph of the cross-corneal diffusion over time for the standard formulation (aqueous) and for four novel timed release formulations.

The second objective was to achieve an equivalent or improved amount of cross-corneal penetration when compared to the aqueous (Phase IIb—0.1% 17-β-estradiol) formulation which has been proven efficacy. FIG. 12 compares the concentration at different time points for the aqueous control formulation and novel formulations. Initial runs were executed for a period of 180 minutes. In all cases, the improved formulation showed some degree of improved cross-corneal penetration when compared to the aqueous Phase IIb formulation. Notably this improvement in concentration crossing the cornea occurred even though the novel timed release formulations contained only twenty to thirty percent of the concentration of active ingredient found in aqueous Phase IIb formulation.

Figure 13:
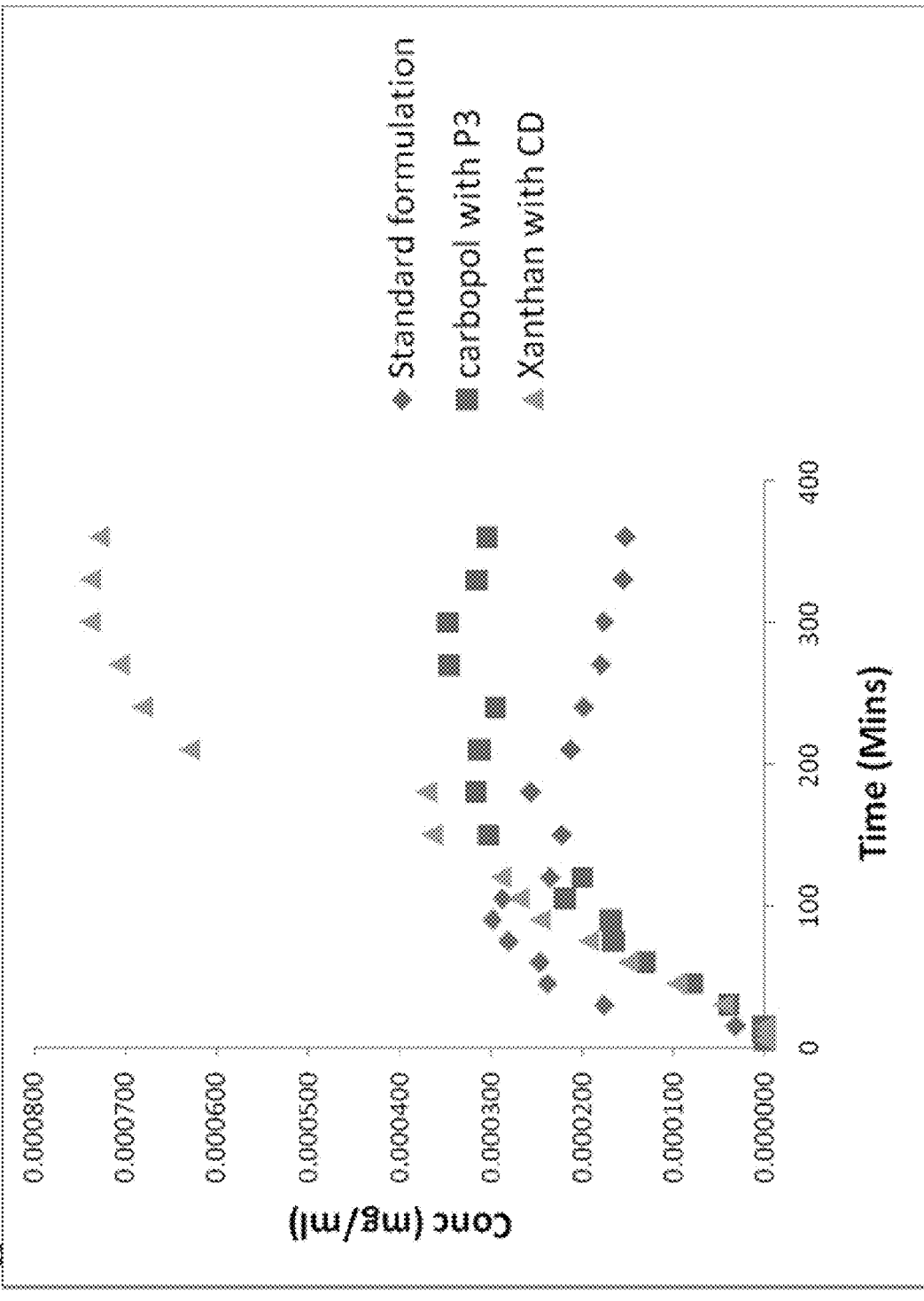
FIG. 13 shows a second graph of the cross-corneal diffusion over time for the standard formulation (aqueous) with the two novel timed release formulations tested for 360 minutes.

The preliminary runs were executed through 180 minutes. Due to the unexpected notable improvements, the third study was executed through 360 minutes. FIG. 13 shows the plot of the formulations that were run for 6 hours. (Note: The data plotted in FIGS. 12 and 14 include the averaged data for all points that had more than one data point available).

FIG. 13 compares the concentration at different time points for the control aqueous formulations and the main novel timed release formulations. The control aqueous formulation shows a rapid increase followed by a slow decline. The timed release formulations containing carbopol-P3 and Xanthan with cyclodextrin were very similar in the earlier phase (first 2 hours) showing a slower build up to a concentration that was similar to the peak concentration of the control aqueous formulation. The timed release carbopol-P3 formulation then stabilized and the concentration was maintained for the duration of the observation period. Predictably, the concentration for the control aqueous formulation declined after its peak. The performance for the timed release formulation of Xanthan with cyclodextrin was quite remarkable: it was still demonstrating increasing concentrations for the whole observation period.

In terms of Area Under the Curve (AUC), if the control aqueous formulation is taken as standard as allocated a value of 1 for AUC, then the value for the timed release carbopol-P3 formulation was 1.21, while that for the timed release Xanthan gum with cyclodextrin formulation was 2.18.

If the concentrations of the formulations were identical, then the result would be similar to those reported for timolol. A different picture develops when one takes the concentration of the test formulations into account. The concentration of the timed release carbopol-P3 formulation was 0.033% 17-β-estradiol making the relative bioavailability in this model 3.6 times that for the control aqueous formulation. The timed release Xanthan gum with cyclodextrin formulation with its concentration of 0.016% 17-β-estradiol has a relative bioavailability of 13.63 compared to the standard formulation! If these results are reproduced in the clinical setting as expected, the timed release Xanthan with cyclodextrin formulation would have a relatively bioavailability that is an amazing 13-14 times that for the standard formulation!

Results—Objective 3

The third objective was to reduce the peak amount of 17-β-estradiol being eliminated through the nasolacrimal drainage system, which can be shown by a slower rate of erosion in the Franz Cell model.

Figure 14:
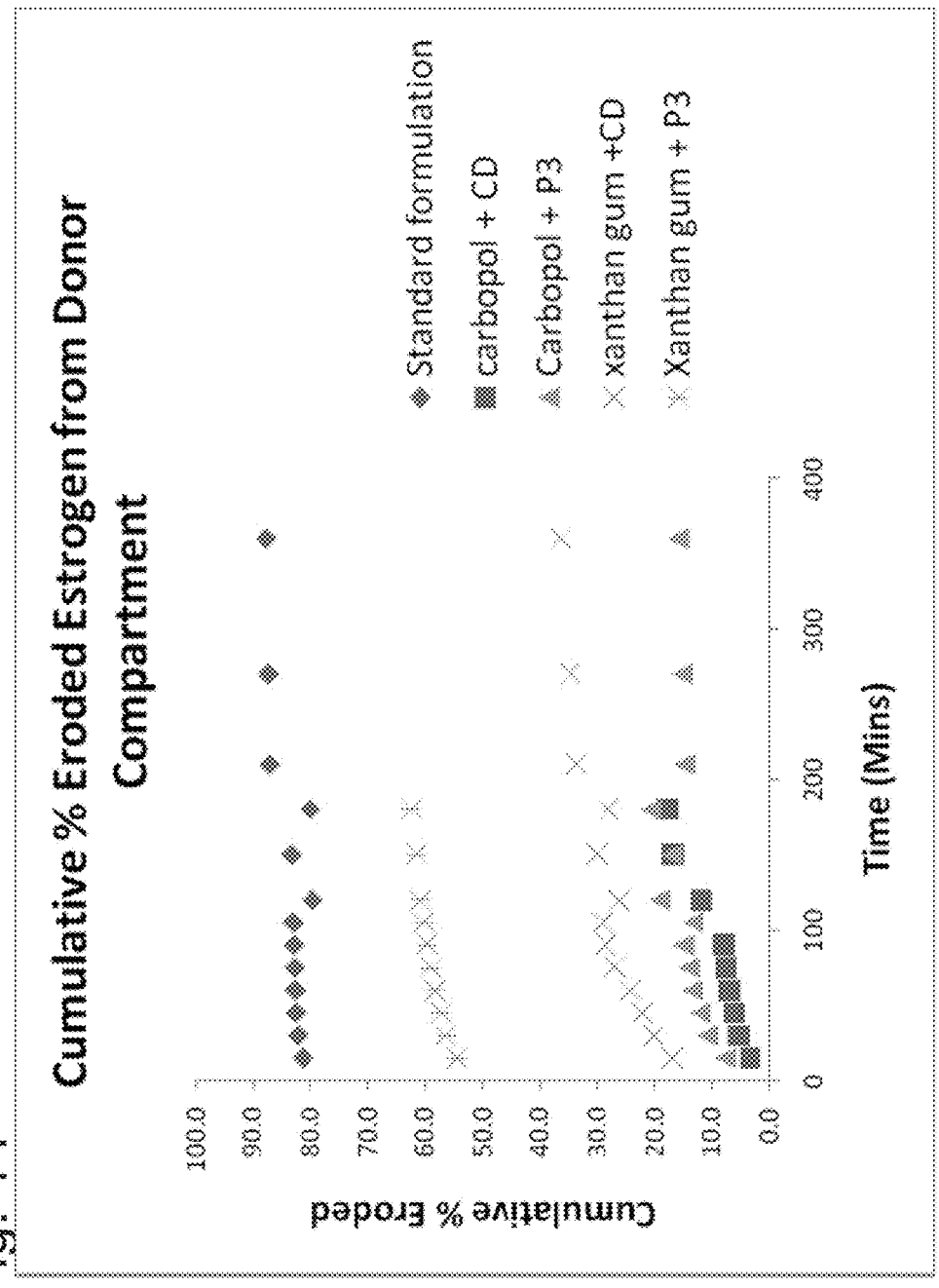
FIG. 14 shows a graph of the cumulative percent eroded estradiol over time for the standard formulation (aqueous) and for four novel timed release formulations.

As discussed under objective 1 above, the aqueous formulation from the Phase IIb trial loses on average 74% of the applied dose (greater than 80%, in one run) within the first fifteen minutes of application. FIG. 14 presents a comparison of erosion data for all formulations tested. This analysis plots the cumulative percent of drug that is found exiting the diffusion erosion chamber. This data models the concentrations of drug one expects to be eliminated through both reflux and normal tear flow.

The data confirmed the rapid erosion of almost 90% of the aqueous control formulation compared with the timed release formulations being tested. In clinical trials, the aqueous control formulation led to a peak systemic concentration of 102 pg/ml in post-menopausal women with dry eye, an increase of approximately 97 pg/ml over baseline values. Extrapolating from the Franz cell model, the increase in peak blood estradiol concentration would be approximately 6 pg/ml with the timed release Xanthan with cyclodextrin formulation and approximately 3.6 pg/ml for the timed release carbopol with cyclodextrin formulation. The normal in post-menopausal women is approximately 13 pg/ml. In the clinical trials the baseline value for estradiol in post-menopausal women with dry eyes was approximately 5 pg/ml. Thus, using either of these novel timed release formulations would not raise blood estradiol levels above the normal value.

CONCLUSION

In this Example 7, a number of novel timed release formulations were tested and compared with the standard aqueous formulation used in the clinical studies discussed in Example 2 above. The novel formulations containing cyclodextrin with Xanthan or carbopol achieved all the desired goals.

The residence time on the ocular surface, represented in this model by the concentration of estradiol in the erosion solution, showed the timed release Xanthan with cyclodextrin formulation to be superior to the standard aqueous formulation over at least 3 hours. The timed release carbopol formulations were even better than this.

With respect to corneal penetration, the timed release carbopol with cyclodextrin formulation achieved a similar concentration as the standard aqueous formulation. Unlike for the control aqueous formulation, these concentrations were maintained for the duration of the studies with no evidence of any decline. This was not expected. The timed release formulation of Xanthan gum with cyclodextrin achieved outstanding corneal penetration concentrations which surprisingly were still increasing six hours after instillation! Taking into account the concentration of the formulations used, and using the AUC for these products, the relative penetration is >3× and 13× that for the standard for the timed release carbopol with cyclodextrin and the Xanthan gum with cyclodextrin formulations, respectively.

The data confirmed that for the aqueous formulation approximately 90% of the delivered dose is eroded with most of the erosion occurring within the first 15 minutes. The timed release Xanthan gum with cyclodextrin formulation showed a cumulative erosion that never exceeded 35% with most of this occurring in the first 2 hours. The erosion data for the timed release carbopol with cyclodextrin formulation is even more impressive at approximately 10%, mostly within the first 2 hours. These values indicated that in clinical use, any increases in estradiol levels will be minimal and should not exceed normal values.

The lowest concentration was that tested for the timed release Xanthan gum with cyclodextrin formulation which had 0.016% 17-β-estradiol. Given the high corneal penetration achieved by this timed release formulation, it is likely that significantly lower concentrations than this will achieve similar efficacy as that reported for 0.1% 17-β-estradiol aqueous formulation. With concentrations as low as 0.005% 17-β-estradiol in the optimal timed release formulations, one should achieve similar corneal penetration as the aqueous formulation at the efficacious 0.1% 17-β-estradiol concentration.

What is claimed is:

1. A method of treating kerato-conjunctivitis sicca (dry eye syndrome) comprising:
    topically administering to an eye, twice daily or less frequently, a drop of a composition comprising:
        i. between about 0.005% and 5% weight-by-weight of estrogen or an estrogen analog or other estrogen receptor modulator; and
        ii. a thermosetting poloxamer or polyethylene glycol gel which is a clear physiologically acceptable solution at room temperature or lower but which forms a gel when placed in the eye,
    wherein the composition has a sustained drug release rate which delivers a dose of between 0.1 mg/ml and 1.0 mg/ml of estrogen or estrogen analog per hour for at least about 6-8 hours after application, as measured by a Franz diffusion cell model with simulated tear flow.

2. The method of claim 1, wherein the estrogen or an estrogen analog or other estrogen receptor modulator is at a concentration of between about 0.005% and less than 0.05% weight-by-weight in the composition.

3. The method of claim 1, wherein the composition is administered twice daily.

4. The method of claim 1, wherein the volume of the drop is less than 35 µl.

5. The method of claim 1, wherein the drop comprises 35 micrograms or less of the estrogen or an estrogen analog or other estrogen receptor modulator.

6. The method of claim 1, wherein the kerato-conjunctivitis sicca is associated with post-menopause, premature ovarian failure, post-operative refractive surgery or a corneal transplant.

7. The method of claim 1, wherein the estrogen or an estrogen analog or other estrogen receptor modulator is 17-β-estradiol.

8. The method of claim 1, wherein the thermosetting gel comprises polyethylene glycol.

9. The method of claim 1, wherein the thermosetting gel comprises poloxamer.

10. The method of claim 1, wherein the thermosetting gel comprises polyethylene glycol and poloxamer.

* * * * *